(12) United States Patent
Naso et al.

(10) Patent No.: US 8,540,992 B2
(45) Date of Patent: Sep. 24, 2013

(54) METHODS AND VECTORS FOR GENERATING ASIALYLATED IMMUNOGLOBULINS

(76) Inventors: Michael Naso, Radnor, PA (US); T. Shantha Raju, Radnor, PA (US); Bernard Scallon, Radnor, PA (US)

( * ) Notice: Subject to any disclaimer, the term of this patent is extended or adjusted under 35 U.S.C. 154(b) by 413 days.

(21) Appl. No.: 12/521,417

(22) PCT Filed: Dec. 26, 2007

(86) PCT No.: PCT/US2007/088809
§ 371 (c)(1),
(2), (4) Date: Feb. 23, 2010

(87) PCT Pub. No.: WO2008/083150
PCT Pub. Date: Jul. 10, 2008

(65) Prior Publication Data
US 2010/0172911 A1    Jul. 8, 2010

Related U.S. Application Data

(60) Provisional application No. 60/882,301, filed on Dec. 28, 2006.

(51) Int. Cl.
*A61K 39/395* (2006.01)
*C12N 9/00* (2006.01)
*C12N 1/20* (2006.01)
*C12N 15/00* (2006.01)

(52) U.S. Cl.
USPC ............... 424/141.1; 435/183; 435/252.3; 435/320.1; 435/455; 536/23.2

(58) Field of Classification Search
None
See application file for complete search history.

(56) References Cited

U.S. PATENT DOCUMENTS 5,275,939 A    1/1994  Sugimori et al.
7,026,152 B2 *  4/2006  Ingram et al. ............. 435/210

FOREIGN PATENT DOCUMENTS

| WO | WO 99/54342 A1 | 10/1999 |
| WO | WO 2004/003176 A2 | 1/2004 |
| WO | WO 2004/047735 A2 | 6/2004 |
| WO | WO 2005/016455 A2 | 2/2005 |

OTHER PUBLICATIONS

Christensen et al. Biotechnol Appl Biochem. Jun. 2005;41(Pt 3):225-31 (abstract).*
Chica et al. Curr Opin Biotechnol. Aug. 2005;16(4):378-84.*
Sen et al. Appl Biochem Biotechnol. Dec. 2007;143(3):212-23.*
Hanauer. Aliment Pharmacol Ther. Sep. 1999;13 Suppl 4:16-22; discussion 38.*
PCT International Search Report dated Sep. 12, 2008.
Dalziel, et al., "Lectin analysis of human immunoglobulin G N-glycan sialylation," Glycoconjugate Journal, 16: 801-807 (1999).
Scallon, et al., "Higher levels of sialylated Fc glycans in immunoglobulin G molecules can adversely impact functionality," Molecular Immunology, 44: 1524-1534 (2007).
Supplementary European Search Report dated Dec. 17, 2010.
Bäckström, et al., "Recombinant MUC1 mucin with a breast cancer-like O-glycosylation produced in large amounts in Chinese-hamster ovary cells," Biochemical Journal, 376: 677-686 (2003).
Christensen, et al., "Cloning, expression and characterization of a sialidase gene from *Arthrobacter ureafaciens*," Biotechnology and Applied Biochemistry, 41, 225-231 (2005).
Davis, et al., "Active influence virus neuraminidase is expressed in monkey cells from cDNA cloned in simian virus 40 vectors," Proceedings of the National Academy of Science USA, 80(13): 3976-3980 (1983).
Eisenberg, et al., "The therapeutic potential of anti-CD20. What do B-cells do?," Clinical Immunology, 117: 207-213 (2005).
Ferrari, et al., "Cloning and expression of a soluble sialidase from Chinese hamster ovary cells: sequence alignment similarities to bacterial sialidases," Glycobiology, 4(3): 367-373 (1994).
GenBank Accession No. AAQ03260, Aug. 13, 1990.
Geletka, et al., "Infliximab for the treatment of early rheumatoid arthritis," Expert Opinions in Biological Therapy, 5: 405-417 (2005).
He, et al., "Purification and Characterization of Recombinant, Human Acid Ceramidase," The Journal of Biological Chemistry, 278(35): 32978-32986 (2003).
Idusogie, et al., "Mapping of the C1q Binding Site on Rituxan, a Chimeric Antibody with a Human IgG1 Fc," Journal of Immunology, 164: 4178-4184 (2000).
Jefferis, et al., "IgF-Fc-mediated effector functions: molecular definition of interaction sites for effector ligans and the role of glycosylation," Immunological Reviews, 163: 59-76 (1998).
Lifely, et al., "Glycosylation and biological activity of CAMPATH-1H expressed in different cell lines and grown under different culture conditions," Glycobiology, 5(8): 813-822 (1995).
Leonard Presta, "Antibody Engineering for Therapeutics," Current Opinion in Structural Biology, 13(4): 519-525 (2003).
Raju, et al., "Species-Specific Variation in Glycosylation of IgG: Evidence for the Species-Specific Sialylation and Branch-Specific Galactosylation and Importance for Engineering Recombinant Glycoprotein Therapeutics," Glycobiology, 10(5):477-486 (2000).
Richard J. Stockert, "The Asialoglycoprotein Receptor: Relationships Between Structure, Function, and Expression," Physiological Reviews, 75(3): 591-609 (1995).
Wright, et al., "Effect of Glycosylation on Antibody Function: Implications for Genetic Engineering," Trends in Biotechnology, 15(1):26-32 (1997).

* cited by examiner

*Primary Examiner* — Christian Fronda
(74) *Attorney, Agent, or Firm* — Eric Dichter

(57) ABSTRACT

The properties of an Fc-containing protein, for example, an antibody, are controlled by altering the sialylation of the oligosaccharides in the Fc region by transfecting the cell line expressing the Fc-containing protein with a vector sequence encoding a sialidase. The modified Fc-containing proteins have therapeutic utility in diseases or conditions in which it is desirable to control the affinity for one or more of the FcγRI, FcγRIIA, and FcγRIIIA receptors, ADCC activity, macrophage or monocyte activation, serum half-life, and avidity.

3 Claims, 15 Drawing Sheets

Fuc = fucosyl; Gal = galactosyl; Glc = glucosyl; GlcNAc = N-acetylglucosaminyl; Man = mannosyl; and Sia* = sialyl (NANA, N-acetylneuraminyl).

*Sia, sialic acid, which is typically NANA, 5-N-acetylneuraminic acid, (NeuAc) or NGNA, 5-N- glycolylneuraminic acid (NeuGc). Other sialic acids have been found or can be chemically synthesized.

Legend same as for Fig. 1

A)

B)

A)

B)

METHODS AND VECTORS FOR GENERATING ASIALYLATED IMMUNOGLOBULINS

CROSS-REFERENCE TO RELATED APPLICATIONS

This application is a 371 national stage of International Application Number PCT/US2007/088809, filed 26 Dec. 2007, which claims the benefit of U.S. Provisional Application Ser. No. 60/882,301, filed 28 Dec. 2006. The entire contents of each of the aforesaid applications are incorporated herein by reference in their entireties.

BACKGROUND OF THE INVENTION

1. Field of the Invention

The invention relates to methods of producing therapeutic proteins that interact with Fc receptors, e.g., antibodies, wherein the composition of the oligosaccharide chains are optimized for avidity of the antibody for its target as well as the Fc receptor binding affinity thereby optimizing the effector function activity of said antibodies as compared to non-optimized methods of producing glycosylated antibodies.

2. Description of the Related Art

Antibodies are soluble serum glycoproteins that play a significant role in innate immunity. The carbohydrate structures of all naturally produced antibodies at conserved positions in the heavy chain constant regions varies with isotype. Each isotype possesses a distinct array of N-linked oligosaccharide structures, which variably affect protein assembly, secretion or functional activity (Wright, A., and Morrison, S. L., Trends Biotech. 15:26-32 (1997)). Referring to FIGS. 1 & 2, the structure of the attached N-linked oligosaccharides varies considerably, depending on the degree of processing, and can include high-mannose, as well as complex biantennary oligosaccharides with or without bisecting GlcNAc and core Fucose residues (Wright, A., and Morrison, S. L., supra). Typically, there is heterogeneous processing of the core oligosaccharide structures attached at a particular glycosylation site such that even monoclonal antibodies exist as multiple glycoforms. Likewise, it has been shown that major differences in antibody glycosylation occur between antibody-producing cell lines, and even minor differences are seen for a given cell line grown under different culture conditions.

Sialic acid on glycans (static groups) are known to be important in prolonging the serum half-life of glycoproteins other than antibodies (Stockert, R. J. (1995) *Physiol. Rev.* 75, 591-609). Thus far, the role of sialic acid on monoclonal antibodies (Mabs) is not well understood. The serum half-life of Mabs is particularly long-lived and construction of Fc-fusion proteins has proved a useful strategy in developing therapeutic proteins, e.g., the protein enteracept.

Antibodies and T-cell receptor molecules possess regions that are responsible for specific cell surface receptor binding, which binding modulates the cellular response. In the immune system, these functions are classified as humoral and cellular. Antibodies are often referred to as adaptor molecules linking humoral and cellular immune mechanisms: humoral responses being attributed mainly to mature, secreted, circulating antibodies capable of high affinity binding to a target antigen. Cellular responses are attributed to the consequences of cellular activation by binding of ab-ag complexes and by downstream sequelae caused by the release of cell mediators as a result of ab-ag complex binding to effector cells. These cellular responses include neutralization of target, opsonization and sensitization (if antigen is displayed on the surface of a cell), sensitization of mast cells, and activation of complement. For cellular targets, that is, cell surface antigens, these effector functions lead to what is commonly known as antibody-dependent cellular cytotoxicity (ADCC) and complement-dependent cytotoxicity (CDC).

Among antibody isotypes (e.g., IgE, IgD, IgA, IgM, and IgG), IgGs are the most abundant with the IgG1 subclasses exhibiting the most significant degree and array of effector functions. IgG1-type antibodies are the most commonly used antibodies in cancer immunotherapy where ADCC and CDC activity are often deemed important. Structurally, the IgG hinge region and CH2 domains play a major role in the antibody effector functions. The N-linked oligosaccharides present in the Fc region (formed by the dimerization of the hinge, CH2 and CH3 domains) affect the effector functions. The covalently bound oligosaccharides are complex biantennary type structures and are highly heterogeneous (see FIGS. 1 and 2). A conserved N-linked glycosylation site at Asn297 lies in each CH2 domain. In the mature antibody, the two complex bi-antennary oligosaccharides attached to Asn297 are buried between the CH2 domains, forming extensive contacts with the polypeptide backbone. It has been found that their presence is essential for the antibody to mediate effector functions, such as ADCC (Lifely, M. R., et al., Glycobiology 5:813-822 (1995); Jefferis, R., et al., Immunol Rev. 163:59-76 (1998); Wright, A. and Morrison, S. L., supra).

The heterogeneous oligosaccharides decorating the Fc-portion antibody or antibody-derived structures comprising produced by various host cells contain predominantly sialic acid, fucose, galactose and GlcNAc residues as terminal sugars (Raju, T. S., et al. Glycobiology 2000. 10(5): 477-86). It has been shown that some of these terminal sugars, particularly exposed galactose, core fucose and bisecting GlcNAc residues, affect the structure of the Fc-portion of the molecule and thereby alter antibody effector functions. Effector functions such as ADCC activity and CDC activity which relies on binding to cell surface receptors known as Fc-receptors, as well as the binding to various ligands including C1q complement protein can be altered by the composition of the appended glycan (Presta L. 2003. Curr Opin Struct Biol. 13(4):519-25). The majority of the N-linked glycans attached at the Fc are not sialylated to a significant extent (Idusogie E E, et al. 2000. J Immunol. 15:164(8):4178-84).

The major structures found in human IgG and other recombinantly-produced IgGs are the complex biantennary structures with or without exposed Gal residues (FIG. 1). There are a number of mammalian host cells that are currently used to express recombinant antibodies for research purposes, as well as, biopharmaceutical production. Host cell species of origin as well as culture conditions can cause the extent and structure of glycans appended to recombinantly expressed molecules to vary. Two commonly used host cell lines for the recombinant expression of antibodies are Chinese hamster ovary cells (CHO) and mouse myeloma cells (sp2/0, 653, NS0). While CHO cells express recombinant antibodies which are virtually devoid of sialic acid glycan the glycans are 99% fucosylated. The presence of fucose has been shown to be a major contributor to reduced Fc-gammaIII receptor and therefore ADCC. Mouse myeloma cells express recombinant antibodies with up to 50% sialic acid but with generally less fucose. As stated above, these differences can have significant effects on antibody activity in vivo.

Therefore, it would be desirable to be able to reduce sialylation of glycans associated to therapeutic antibodies in a manner which eliminates the need for post-harvest processing and at the same time provides a reasonably homogeneous structure with respect to sialic acid content.

SUMMARY OF THE INVENTION

The present invention comprises methods, host cell lines, and expression vectors and plasmids useful for producing Fc-containing molecules, particularly antibody therapeutics, with reduced sialic acid content. More particularly, the invention comprises an expression plasmid encoding an engineered sialidase coding sequence, which plasmid once incorporated into an antibody secreting host cell line, causes the host cell to be capable of secreting a polypeptide having sialidase activity. In one embodiment, the coding sequence within the plasmid codes for the catalytic domain of the *Arthrobacter ureafaciens* sialidase. In a further aspect of the invention, the host cell comprising the catalytic domain of the *Arthrobacter ureafaciens* sialidase, secretes the translated catalytic domain into the culture medium.

The present invention comprises a method for controlling the properties of an Fc-containing molecule, comprising minimizing sialylation of the oligosaccharides attached to the Fc region whereby the avidity of the molecule for multiply localized target proteins and the affinity for one or more of the Fc gamma receptors, e.g., FcγRI, FcγRIIA, and FcγRIIIA receptors; ADCC activity; macrophage or monocyte activation; and serum half-life are optimized.

The invention also relates to the preparation of highly homogeneous batches of Fc-containing molecules, such as antibodies, containing maximally sialylated N-linked oligosaccharides in the Fc domain. It further relates to the purification of batches of antibodies enriched for antibodies that contain sialic acid in the Fc oligosaccharide as well as antibodies that do not contain sialic acid in the Fc oligosaccharide.

DETAILED DESCRIPTION OF THE INVENTION

Abbreviations

Figure 1:
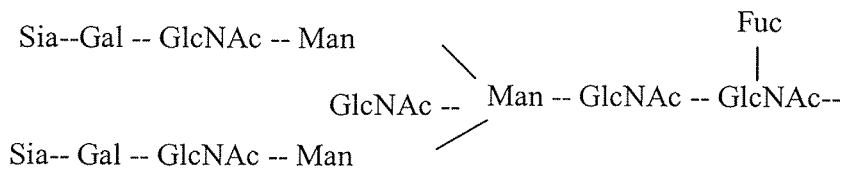
FIG. 1 is a schematic depiction of the largest oligosaccharide structure found in human IgG.
Figure 2:
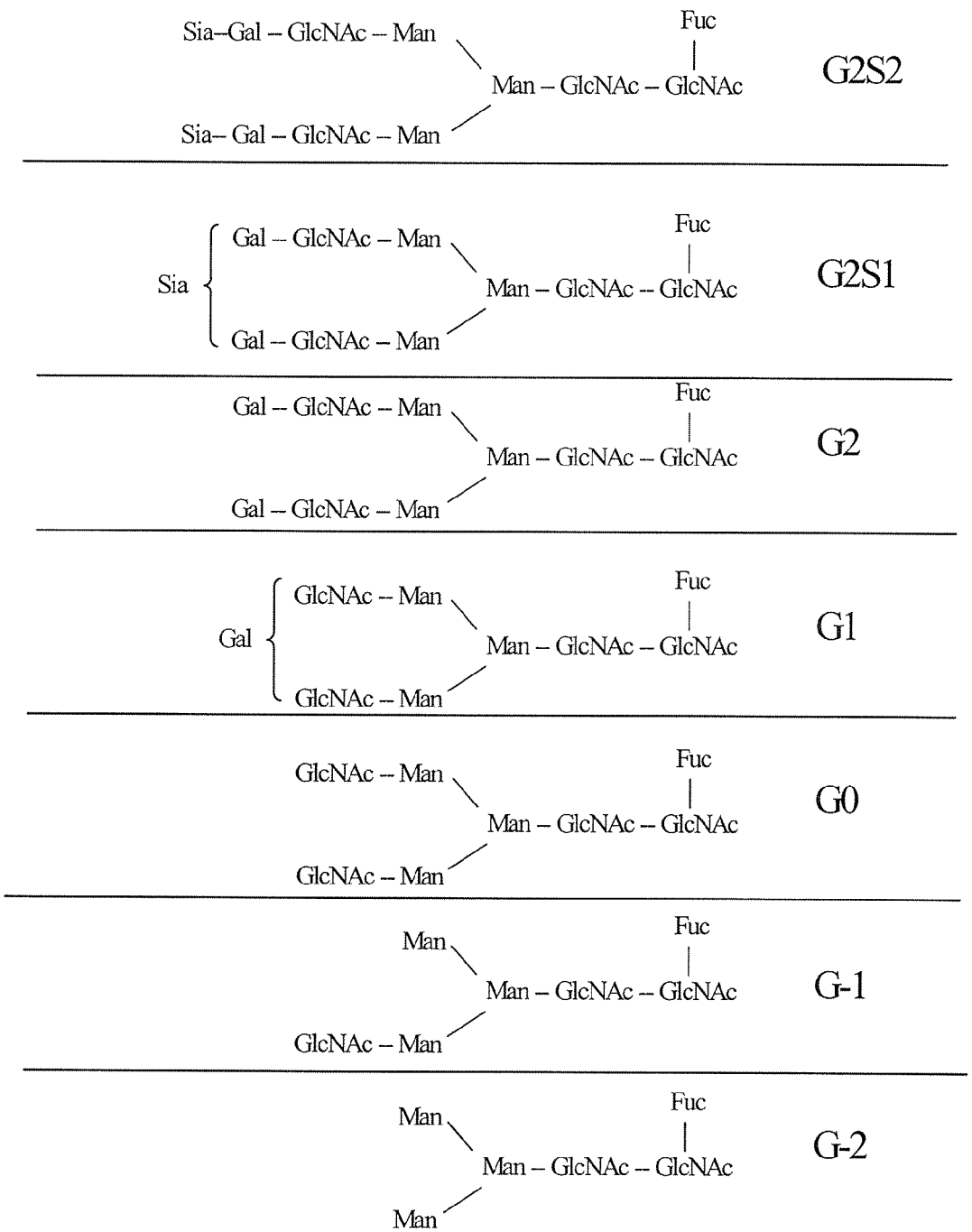
FIG. 2 depicts the major oligosaccharide structures found in a recombinant IgG produced in Chinese hamster ovary (CHO) cells.

α1,3GT, α-1,3-galactosyltransferase; α2,3ST, α-2,3-sialyltransferase; β1,4GT, β-1,4-galactosyltransferase; ADCC, antibody-dependent cellular cytotoxicity; ATCC, American Type Culture Collection; BATDA, bis(acetoxymethyl) 2,2': 6',2"-terpyridine-y,y"-dicarboxylate; BSA, bovine serum albumin; CD medium, chemically-defined culture medium; CDC, complement-directed cytotoxicity; CMP-Sia, cytidine monophosphate N-acetylneuraminic acid; DMEM, Dulbecco's Modified Eagle's media; E:T, effector cell to target cell ratio: FBS, fetal bovine serum; ESI-MS, electrospray ionization mass spectrometry. NK cells, natural killer cells; IgG, immunoglobulin G; IMDM, Iscove's Modified Dulbecco's medium; MALDI-TOF-MS, matrix-assisted laser/desorption ionization time-of-flight mass spectrometry; MHX, mycophenolic acid, hypoxanthine, xanthine.; NANA, N-acetylneuraminic acid isomer of sialic acid; NGNA, N-glycolyl-neuraminic acid isomer of sialic acid; PBMC, peripheral blood mononuclear cells; PBMC, peripherall blood mononuclear cell; PBS, phosphate-buffered saline; PNGase F, peptide Nglycosidase F; RP-HPLC, reversed phase high-performance liquid chromatography; RT, room temperature; Sia, sialic acid; UDP-Gal, uridine diphosphate galactose; UDP-GlcNAc, uridine diphosphate N-acetylglucosamine.

Definitions

The term "ADCC activity" stands for antibody-dependent cell-mediated cytotoxicity and means the phenomenon of antibody-mediated target cell destruction by non-sensitized effector cells. The identity of the target cell varies, but it must have bound surface immunoglobulin G having an Fc-domain or Fc-domain portion capable of Fc-receptor activation. The effector cell is a "killer" cell possessing Fc receptors. It may be, for example, a lymphocyte lacking conventional B- or T-cell markers, or a monocyte, macrophage, or polynuclear leukocyte, depending on the identity of the target cell. The reaction is complement independent. The ADCC activity of an antibody or other Fc-containing protein of the present invention is "enhanced," if its ability to demonstrate ADCC mediated cell killing surpasses the ability of an antibody or protein of substantially similar sequence and Fc-domain produced by an alternative host cell. ADCC activity may be determined in a standard in vivo or in vitro assay of cell killing, such as the assays discussed herein. Preferably, the antibody of the invention having enhanced ADCC activity achieves the same effect (prevention or inhibition of tumor cell growth) at a lower dose and/or in a shorter time than a reference antibody produced in an alternate host cell. Preferably, the difference between the potency of an antibody within the scope of the present invention and a reference antibody is at least about 1.5-fold, more preferably at least about 2-fold, even more preferably, at least about 3-fold, most preferably, at least about 5-fold, as determined, for example, by side-by-side comparison in a selected standard chromium release ADCC assay.

The term "affinity" as used herein is intended to be a measure of the binding constant of a simple monovalent ligand for its cognate binding partner, for example, the binding of a Fab' for an antigen or epitope. Affinity can be measured in several ways including but measuring on- and off-rates ($k_{on}$ and $k_{off}$ respectively) by e.g. plasmon resonance (BiaCore) and expressed as an overall association ($K_{ass}$) or dissociation constant ($K_D$) where $K_{ass}$ is $k_{on}/k_{off}$ and $K_D$ is $k_{off}/k_{on}$. $K_D$ may also be measured empirically by, e.g. measuring the concentration at which binding of the ligand to a binding partner is half-saturated. Another method of measuring $K_D$ is by competition assay, in which one binder or ligand is labeled or tagged and held at a constant concentration while the test binder or ligand is added at varying concentrations to compete away the labeled substance from its cognate binding partner and determining the concentration at which label is diminished by half.

The term "avidity" as used herein is intended to be a measure of the tendency of a ligand to remain bound to a binding partner insofar as both the ligand and the binding partner may be multivalent and the tendency for multiple association and dissociation events can occur simultaneously for a specific ligand. Thus, avidity can be gauged by an increase in apparent affinity of multivalent conformations of a binding partner with a known affinity.

The term "Fc-containing protein" or "Fc-containing molecule" as used herein refers to a monomeric, dimeric or heterodimeric protein having a ligand binding domain and at least an immunoglobulin CH2 and CH3 domain. The CH2 and CH3 domains can form at least a part of the dimeric region of the protein/molecule (e.g., antibody).

The term "antibody" is intended to encompass antibodies, digestion fragments, specified portions and variants thereof, including, without limitation, antibody mimetics or comprising portions of antibodies that mimic the structure and/or function of an antibody or specified fragment or portion thereof, and retain Fc-mediated functions, including but not limited to: binding to Fc-receptors (e.g. FcγRI (CD64) FcγRIIA (CD32A), FcγRIIIA (CD16A) and FcRn), binding complement (e.g. C1q), ADCC and CDC.

The term "monoclonal antibody" as used herein is a specific form of Fc-containing fusion protein in which the ligand binding domain retains substantial homology to at least one of a heavy or light chain antibody variable domain of at least one species of animal antibody.

The "effector functions" of antibodies or antibody analogs as it is used herein are processes by which pathogens or abnormal cells, e.g., tumor cells, are destroyed and removed from the body. Innate and adaptive immune responses use most of the same effector mechanisms to eliminate pathogens including ADCC, CA (complement activation), C1q binding, and opsinization.

As used herein, the term "host cell" refers to any kind of cellular system which can be engineered to generate proteins, protein fragments, or peptides of interest, including antibodies and antibody fragments. Host cells include, without limitation, cultured cells, e.g., mammalian cultured cells, such as CHO cells, BHK cells, NSO cells, SP2/0 cells, or hybridoma cells, yeast cells, and insect cells, but also cells comprised within a transgenic animal or cultured tissue.

The term "sialic acid" refers to any member of a family of nine-carbon carboxylated sugars. The most common member of the sialic acid family is N-acetyl neuraminic acid (2-keto-5-acetamido-3,5-dideoxy-D-glycero-D-galactononulopyranos-1-onic I acid (often abbreviated as Neu5Ac, NeuAc, or NANA). A second member of the family is N-glycolyl-neuraminic acid (NGNA, Neu5Gc or NeuGc), in which the N-acetyl group of NeuAc is hydroxylated. This form is prevalent in glycoproteins from rodent and microbial sources. A third sialic acid family member is 2-keto-3-deoxy-nonu-losonic acid (KDN) (Nadano et al. (1986) J. Biol. Chem. 261: 11550-11557; Kanamori et al., J. Biol. Chem. 265: 21811-21819 (1990)). Also included are 9-substituted sialc acids such as a 9-O—C—C6 acyl Neu5Ac like 9-O-lactyl-Neu5Ac or 9-O-acetyl-Neu5Ac, 9-deoxy-9-fluoro-Neu5Ac and 9 azido-9-deoxy-Neu5Ac. For review of the static acid family, see, e.g., Varki, Glycobiology 2: 25-40 (1992); Sialic Acids: Chemistry, Metabolism and Function, R. Schauer, Ed. (Springer Verlag, New York (1992)).

Description

Whereas the present inventors have unexpectedly found that the level of sialylation of the Fc oligosaccharides alters the affinity of recombinantly-produced therapeutic antibodies for Fcγ receptors, resulting in modulation of various aspects of the biological actions of said antibodies. More specifically, it was discovered that highly sialylated Abs have significantly reduced affinity for the low-affinity receptors, FcγRIIA (CD32A) and FcγRIIIA (CD16A), and have significantly reduced activity in in vitro ADCC assays in which FcγRIIIA is believed to be the relevant receptor. It was further discovered that highly sialylated Abs have increased affinity for the high-affinity Fcγ receptor, FcγRI (CD64), and that fully sialylated Fc-containing proteins have reduced serum half-life as compared to asialylated or partially sialylated Fc-containing proteins. It was further discovered that the removal (or the absence or reduced levels) of sialic acid from the Fc oligosaccharides enhances the avidity of recombinantly-produced therapeutic antibodies for their target molecule. These discoveries and supporting information have been described in co-pending U.S. Provisional Application Nos. 60/695,769, 60/809,106, 60/841,153

While not wishing to be bound to any one theory, the removal of the charged static group from the oligosaccharide can be interpreted as allowing more flexibility in the overall antibody structure, which flexibility imparts an enlarged sphere of potential interaction for the two binding domains in relationship of one to the other. The capacity of an Ab to bind bivalently to two antigen epitopes will also depend on epitope accessibility, orientation, density, and mobility. It should be noted that the antigen binding effect of sialylation may also be relevant to Abs that recognize viral or bacterial surface antigens, and even soluble antigens that are homopolymers, since Ab flexibility can determine to what extent individual Ab molecules bind bivalently within a soluble immune complex, where not only might some of the Abs bind more than one antigen but some of the antigens may be bound by more than one Ab.

The present invention comprises a method for controlling the properties of an Fc-containing molecule by altering the sialylation of the Fc oligosaccharides and the altered Fc-containing molecules. Sialic acid has a net negative charge at physiological pH and, thus, the presence of sialic acid in the Fc-bound carbohydrate might be expected to alter the three-dimensional structure and hence conformation of the CH2 domain and thereby affect Fc binding to various ligands or receptors. The altered Fc-containing molecule affects the affinity for one or more of the FcγRI, FcγRIIA, and FcγRIIIA receptors, ADCC activity, macrophage or monocyte activation, and serum half-life.

Enrichment of Sialylated Forms of Fc-containing Proteins

One approach to prepare sublots of a particular Fc-containing protein that differ in sialic acid content is to take an Fc-containing protein preparation with heterogeneous Fc oligosaccharides, including both sialylated and asialylated molecules, and pass it over a column containing an immobilized lectin that has differential affinity for sialylated and asialylated oligosaccharides. The nonbinding flow-through (T, through) or the column unbound fraction can be separated from the bound fraction (B, bound), the latter collected while passing elution buffer through the column. It may also be possible to separately collect a weakly bound fraction or the column retarded fraction (R, retarded), for example, by collecting Fc-containing protein that elutes during continued washing of the column with the original sample buffer. Depending on the lectin used, the nonbinding fraction may have a higher or lower sialic acid content than the fraction that binds.

Examples of lectins that may enrich for sialylated or asialylated Fc-containing proteins are the lectin from *Maackia amurensis* (MAA), which specifically binds oligosaccharides with terminal sialic acid, and the lectin wheat germ agglutinin (WGA), which specifically binds oligosaccharides with either terminal sialic acid or terminal N-acetylglucosamine (GlcNAc). Another example is the lectin Ricin I (RCA), which binds oligosaccharides with terminal galactose. In the latter example, the non-binding flow-through fraction may be enriched for sialylated Fc-containing molecules.

Enzymatic Modification of Fc-Containing Proteins

An alternative approach for preparing sublots of an Fc-containing protein that differ in sialic acid content is to treat a portion of an Fc-containing protein preparation with sialidase enzyme, thereby removing sialic acids. The resulting asialylated material can be compared to the original, partially sialylated material for differences in biological activity. The higher the sialic acid content in the original Fc-containing protein lot, the greater the chance of detecting any differences in biological activity. For example, if only 10% of the Fc oligosaccharides in the original protein preparation contained sialic acid, it may be difficult to detect differences in biological activity after sialidase treatment, when 0-1% of the oligosaccharides contain sialic acid. Comparing the biological activity of an Fc-containing protein before and after sialidase treatment will be more difficult if sialidase treatment results in a different distribution of fucosylated and afucosylated oligosaccharides, since fucose levels has a profound effect on certain biological activities, such as affinity for human FcγRIIIA and ADCC activity. For example, if a reduction of the sialic acid content from 30% of the oligosaccharides to 0% results in the proportion of afucosylated oligosaccharides increasing from 5% to 15%, then it will not be possible to attribute differences in ADCC activity solely to the decrease in sialic acid content. Such an effect of sialidase treatment on the relative proportion of fucosylated and afucosylated oligosaccharides is possible (and has been observed) because of the difference in the sialylation of fucosylated and afucosylated oligosaccharides prior to the treatment with sialidase to remove sialic acid residues.

Sialylation of oligosaccharides present in the Fc region can also be achieved using in vitro glycosylation methods. Using such methods, it is possible to attain maximally-sialylated glycoforms of antibody samples. Based on the present discovery, maximally-sialylated glycoforms of antibodies or other Fc-containing constructs will have reduced serum half-life as compared to asialylated or under-sialylated antibodies. Thus, the method of the invention provides an optional means for controlling both the homogeneity of the glycoforms comprising antibody or other recombinant protein constructs containing an immunoglobulin Fc region and the in vivo functional aspects of said antibodies or constructs.

Glycosyltransferases naturally function to synthesize oligosaccharides. They produce specific products with excellent stereochemical and regiochemical geometry. The transfer of glycosyl residues results in the elongation or synthesis of an oligo- or polysaccharide. A number of glycosyltransferase types have been described including sialyltransferases, fucosyltransferases, galactosyltransferases, N-acetylgalactosaminyltransferases, N-acetylglucosaminyltransferases and the like.

Glycosyltransferases which are useful in the present invention include, for example, α-sialyltransferases, α-glucosyltransferases, α-galactosyltransferases, α-fucosyl-transferases, α-mannosyltransferases, α-xylosyltransferases, α-N-acetylhexosaminyltransferases, β-sialyltransferases, β-glucosyltransferases, β-galactosyltransferases, β-fucosyltransferases, β-mannosyltransferases, xylosyltransferases, and β-N-acetylhexosaminyltransferases, such as those from *Neisseria meningitidis*, or other bacterial sources, and those from rat, mouse, rabbit, cow, pig, human and insect and viral sources. Preferably, the glycosyltransferase is a truncation variant glycosyltransferase enzyme in which the membrane-binding domain has been deleted.

Exemplary galactosyltransferases include α(1,3) galactosyltransferase (E.C. No. 2.4.1.151, see, e.g., Dabkowski et al., Transplant Proc. 25:2921 (1993) and Yamamoto et al. Nature 345:229-233 (1990)) and α(1,4) galactosyltransferase (E.C. No. 2.4.1.38). Other glycosyltransferases can be used, such as a sialyltransferase.

An α(2,3)sialyltransferase, often referred to as the sialyltransferase, can be used in the production of sialyl lactose or higher order structures. This enzyme transfers sialic acid (NeuAc) from CMP-sialic acid to a Gal residue with the formation of an α-linkage between the two saccharides. Bonding (linkage) between the saccharides is between the 2-position of NeuAc and the 3-position of Gal. An exemplary α(2,3)sialyltransferase referred to as α(2,3)sialyltransferase (EC 2.4.99.6) transfers sialic acid to the non-reducing terminal Gal of a Galβ 1→3Glc disaccharide or glycoside. See, Van den Eijnden et al., J. Biol. Chem., 256:3159 (1981), Weinstein et al., 3. Biol. Chem., 257:13845 (1982) and Wen et al., J. Biol. Chem., 267:21011 (1992). Another exemplary α-2,3-sialyltransferase (EC 2.4.99.4) transfers sialic acid to the non-reducing terminal Gal of the disaccharide or glycoside. See, Rearick et al., J. Biol. Chem., 254:4444 (1979) and Gillespie et al., J. Biol. Chem., 267:21004 (1992). Further exemplary enzymes include Gal-β-1,4-GlcNAc α-2,6 sialyltransferase (See, Kurosawa et al. Eur. J. Biochem. 219: 375-381 (1994)).

Other glucosyltransferases particularly useful in preparing oligosaccharides of the invention are the mannosyltransferases including α(1,2) mannosyltransferase, α(1,3) mannosyltransferase, β(1,4) mannosyltransferase, Dol-P-Man synthase, OCh1, and Pmt1.

Still other glucosyltransferases include N-acetylgalactosaminyltransferases including α(1,3) N-acetylgalactosaminyltransferase, β(1,4) N-acetylgalactosaminyltransferases (Nagata et al. J. Biol. Chem. 267:12082-12089 (1992) and Smith et al. J. Biol Chem. 269:15162 (1994)) and polypeptide N-acetylgalactosaminyltransferase (Homa et al. J. Biol Chem. 268:12609 (1993)). Suitable N-acetylglucosaminyltransferases include GnTI (2.4.1.101, Hull et al., BBRC 176: 608 (1991)), GnTII, and GnTIII (Ihara et al. J. Biolchem. 113:692 (1993)), GnTV (Shoreiban et al. J. Biol. Chem. 268: 15381 (1993)).

For those embodiments in which the method is to be practiced on a commercial scale, it can be advantageous to immobilize the glycosyl transferase on a support. This immobilization facilitates the removal of the enzyme from the batch of product and subsequent reuse of the enzyme. Immobilization of glycosyl transferases can be accomplished, for example, by removing from the transferase its membrane-binding domain, and attaching in its place a cellulose-binding domain. One of skill in the art will understand that other methods of immobilization could also be used and are described in the available literature.

Because the acceptor substrates can essentially be any monosaccharide or oligosaccharide having a terminal saccharide residue for which the particular glycosyl transferase exhibits specificity, substrate may be substituted at the position of its non-reducing end. Thus, the glycoside acceptor may be a monosaccharide, an oligosaccharide, a fluorescent-labeled saccharide, or a saccharide derivative, such as an aminoglycoside antibiotic, a ganglioside, or a glycoprotein including antibodies and other Fc-containing proteins. In one group of preferred embodiments, the glycoside acceptor is an oligosaccharide, preferably, Galβ(1-3)GlcNAc, Galβ(1-4) GlcNAc, Galβ(1-3)GalNAc, Galβ(1-4)GalNAc, Man α(1,3) Man, Man α(1,6)Man, or GalNAcβ(1-4)-mannose. In a particular preferred embodiment, the oligosaccharide acceptor is attached to CH2 domain of an Fc-containing protein.

The use of activated sugar substrate, i.e. sugar-nucleoside phosphate, can be circumvented by either using a regenerating reaction concurrently with the glycotransferase reaction (also known as a recycling system). For example, as taught in, e.g., U.S. Pat. No. 6,030,815, a CMP-sialic acid recycling system utilizes CMP-sialic acid synthetase to replenish CMP-sialic acid (CMP-NeuAc) as it reacts with a sialyltransferase acceptor in the presence of a α(2,3)sialyltransferase to form the sialyl-saccharide. The CMP-sialic acid regenerating system useful in the invention comprises cytidine monophosphate (CMP), a nucleoside triphosphate (for example adenosine triphosphate (ATP), a phosphate donor (for example, phosphoenolpyruvate or acetyl phosphate), a kinase (for example, pyruvate kinase or acetate kinase) capable of transferring phosphate from the phosphate donor to nucleoside diphosphates and a nucleoside monophosphate kinase (for example, myokinase) capable of transferring the terminal phosphate from a nucleoside triphosphate to CMP. The α(2, 3)sialyltransferase and CMP-sialic acid synthetase can also be viewed as part of the CMP-sialic acid regenerating system as removal of the activated sialic acid serves to maintain the forward rate of synthesis. The synthesis and use of sialic acid compounds in a sialylation procedure using a phagemid comprising a gene for a modified CMP-sialic acid synthetase enzyme is disclosed in international application WO 92/16640, published Oct. 1, 1992.

An alternative method of preparing oligosaccharides is through the use of a glycosyltransferase and activated glycosyl derivatives as donor sugars obviating the need for sugar nucleotides as donor sugars as taught in U.S. Pat. No. 5,952, 203. The activated glycosyl derivatives act as alternates to the naturally-occurring substrates, which are expensive sugar-nucleotides, usually nucleotide diphosphosugars or nucleotide monophosphosugars in which the nucleotide phosphate is α-linked to the 1-position of the sugar.

Activated glycoside derivatives which are useful include an activated leaving group, such as, for example, fluoro, chloro, bromo, tosylate ester, mesylate ester, triflate ester and the like. Preferred embodiments of activated glycoside derivatives include glycosyl fluorides and glycosyl mesylates, with glycosyl fluorides being particularly preferred. Among the glycosyl fluorides, α-galactosyl fluoride, α-mannosyl fluoride, α-glucosyl fluoride, α-fucosyl fluoride, α-xylosyl fluoride, α-sialyl fluoride, alpha-N-acetylglucosaminyl fluoride, α-N-acetylgalactosaminyl fluoride, β-galactosyl fluoride, β-mannosyl fluoride, β-glucosyl fluoride, β-fucosyl fluoride, β-xylosyl fluoride, beta-sialyl fluoride, β-N-acetylglucosaminyl fluoride and β-N-acetylgalactosaminyl fluoride are most preferred.

Glycosyl fluorides can be prepared from the free sugar by first acetylating the sugar and then treating it with HF/pyridine. Acetylated glycosyl fluorides may be deprotected by reaction with mild (catalytic) base in methanol (e.g. NaOMe/ MeOH). In addition, many glycosyl fluorides are commercially available. Other activated glycosyl derivatives can be prepared using conventional methods known to those of skill in the art. For example, glycosyl mesylates can be prepared by treatment of the fully benzylated hemiacetal form of the sugar with mesyl chloride, followed by catalytic hydrogenation to remove the benzyl groups.

A further component of the reaction is a catalytic amount of a nucleoside phosphate or analog thereof. Nucleoside monophosphates which are suitable for use in the present invention include, for example, adenosine monophosphate (AMP), cytidine monophosphate (CMP), uridine monophosphate (UMP), guanosine monophosphate (GMP), inosine monophosphate (IMP) and thymidine monophosphate (TMP). Nucleoside triphosphates suitable for use in accordance with the present invention include adenosine triphosphate (ATP), cytidine triphosphate (CTP), uridine triphosphate (UTP), guanosine triphosphate (GTP), inosine triphosphate (ITP) and thymidine triphosphate (TTP). A preferred nucleoside triphosphate is UTP. Preferably, the nucleoside phosphate is a nucleoside diphosphate, for example, adenosine diphosphate (ADP), cytidine diphosphate (CDP), uridine diphosphate (UDP), guanosine diphosphate (GDP), inosine diphosphate (IDP) and thymidine diphosphate (TDP). A preferred nucleoside diphosphate is UDP. As noted above, the present invention can also be practiced with an analog of the nucleoside phosphates. Suitable analogs include, for example, nucleoside sulfates and sulfonates. Still other analogs include simple phosphates, for example, pyrophosphate.

One procedure for modifying recombinant proteins produced, in e.g., murine cells wherein the hydroxylated form of sialic acid predominates (NGNA), is to treat the protein with sialidase, to remove NGNA-type sialic acid, followed by enzymatic galactosylation using the reagent UDP-Gal and beta1,4 Galtransferase to produce highly homogeneous G2 glycoforms. The preparation can then, optionally, be treated with the reagent CMP-NANA and alpha-2,3 sialyltransferase to give highly homogeneous G2S2 glyoforms.

Where the removal or elimination of sialic acid groups from the glycans appended to the Fc-region of antibodies or Fc-containing molecules is desired, a sialidase can be used. A number of sialidases of varying specificity are known in the literature. A soluble CHO cell sialidase has been identified (Ferrari et al, 1994, Glycobiology 4:367-373) and, if leaked into the culture medium may be responsible for the extracellular removal on sialic on glycans of recombinant proteins. Thus, it is possible that addition and removal of sialic acid groups can occur during the production of recombinant proteins which may account for the variable and heterogeneous glycan structures on proteins produced by CHO cell lines.

Sialidases (neuraminidases) have been isolated and cloned from a variety of species from bacteria to man with varying specificities for substrates, e.g. glycoproteins, glycolipids, and gangliosides and linkages. Enzymes with broad specificity for the type of static group, e.g. hydroxylated (NGNA) or non-hydroxylated neuraminic acids and linkages which may be α2,3-, α2,6-, or α2,8- and branched sialic acids linked to an internal residue; include those from Clostridium perfringens and sialidases from *Arthrobacter ureafaciens* (sialidase A, N-acetylneuraminate glycobyhdroalse; EC 3.2.1.18). Purified enzymes are available commercially from, e.g. Prozyme, Inc, San Leandro, Calif. The nucleotide sequence of *A ureafaciens* sialidase gene has been cloned (NCBI Accession No. AY934539) by Lundbeck et al. 2005. Biotechnolo. Appl. Bochem 41:225-231.

Using the methods well known in the art, host cells secreting enzymes capable of acting upon extracellular oligosaccharides can be constructed as taught in e.g. U.S. Pat. No. 7,026,152 for cultures capable of production of ethanol by fermentation sugars released by secreted endoglucanases. Lundbeck et al. (supra) expressed a truncated form sialidase A, which was capable of removing sialic acid residues from recombinant erythropoietin muteins. The engineering of a mammalian host cell capable of expression of an therapeutic antibody or other Fc-containing protein and simultaneous desialylation of that expressed protein in the extracellular medium has not been demonstrated. Applicants' present invention demonstrates that the soluble form of sialidase A can be co-expressed by antibody producing cells, and the resulting antibody product recovered from cultures of such cells have reduced sialic acid content in their Fc-portion the molecules. The sialic acid optimized antibodies so produced have enhanced ADCC activity as compared to antibodies produced by conventional cell lines.

Structural Characterization of Sialic Acid Variants

Figure 3:
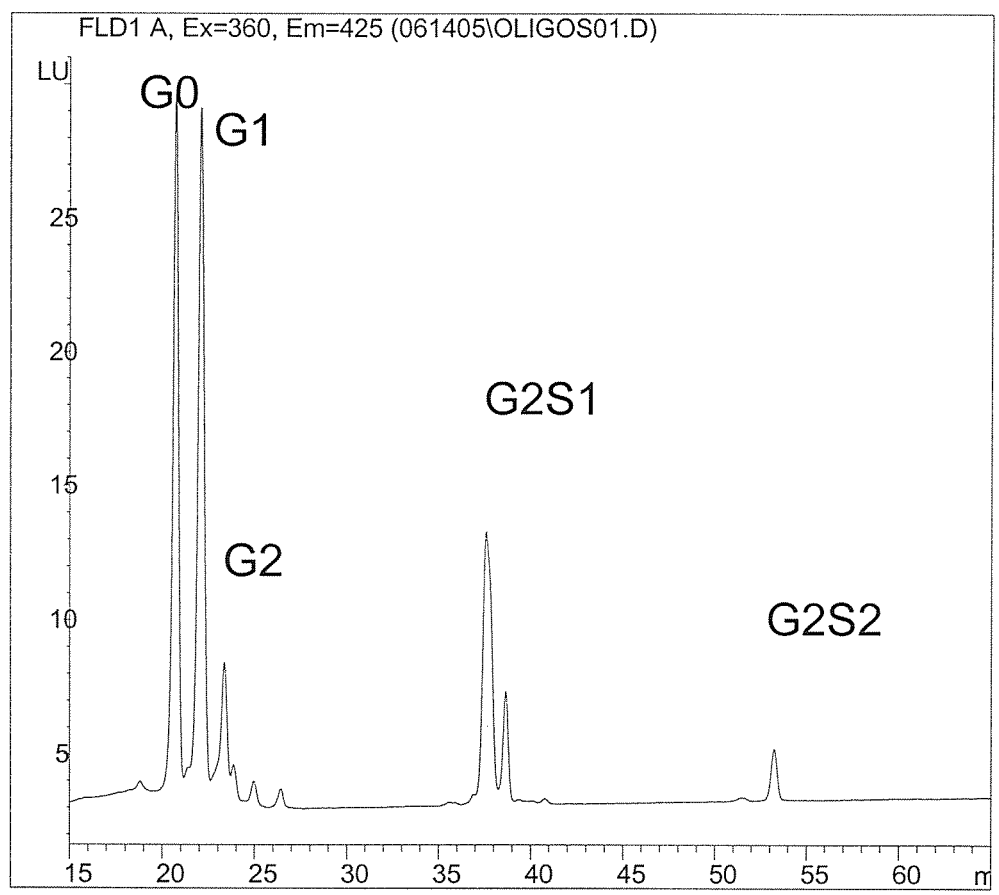
FIG. 3 shows the results of an HPLC analysis of Fc oligosaccharides. The N-linked oligosaccharides were first released from antibody by treating with PNGase F enzyme. The released oligosaccharides were labeled with anthranilic acid and the labeled oligosaccharides were purified by gel-filtration chromatography. The purified labeled oligosaccharides were analyzed by HPLC, resulting in the chromatogram shown.

For structural characterization of sialic acid variants containing oligosaccharides, the glycoprotein preparations including antibody preparations were treated with peptide-N-glycosidase F to release the N-linked oligosaccharides. The enzyme peptide-N-glycosidase F (PNGase F) cleaves asparagines-linked oligosaccharides. The released oligosaccharides were fluorescently labeled with anthranilic acid (2-aminobenzoic acid), purified and analyzed by HPLC as described (see Anumula, K. R. and Dhume S T Glycobiology. 1998 July; 8(7):685-94). As shown in FIG. 3, the oligosaccharides separated as G0, G1, G2, G2S1 and G2S2 in the chromatogram can be detected and quantitated. Aglycosylated species, naturally devoid of glycans or having been chemically or enzymatically stripped of glycan are designated Gno.

Biological Characterization of Sialic Acid Variants

Fc-containing proteins can be compared for functionality by several well-known in vitro assays. In particular, affinity for members of the FcγRI, FcγRII, and FcγRIII family of Fcγ receptors is of interest. These measurements could be made using recombinant soluble forms of the receptors or cell-associated forms of the receptors. In addition, affinity for FcRn, the receptor responsible for the prolonged circulating half-life of IgGs can be measured, for example by BIAcore using recombinant soluble FcRn. Cell-based functional assays, such as ADCC assays and CDC assays, provide insights into the likely functional consequences of particular variant structures. In one embodiment, the ADCC assay is configured to have NK cells act as the primary effector cell, thereby reflecting the functional effects on the FcγRIIIA receptor. Phagocytosis assays may also be used to compare immune effector functions of different variants, as can assays that measure cellular responses, such as superoxide or inflammatory mediator release.

Affinity and Avidity Assays

Antibodies, which are naturally multivalent, can be tested to determine various parameters of binding to target proteins. A convenient format for determining an apparent Kd is the ELISA (enzyme-linked immunosorbent assay) or RIA (radio-immunoassay). "ELISA" has become generally used to mean a binding assay performed on a solid support using indirect detection methods. Generally, in an ELISA, soluble analytes are removed from solution after specifically binding to solid-phase reactants. In the method, solid-phase reactants are prepared by adsorbing an antigen or antibody onto plastic microtiter plates; in other methods, the solid-phase reactants are cell-associated molecules. In all protocols, the solid-phase reagents are incubated with secondary or tertiary reactants covalently coupled to an enzyme. Unbound conjugates are removed by washing and a chromogenic or fluorogenic substrate is added. As the substrate is hydrolyzed by the bound enzyme conjugate, a colored or fluorescent product is generated. Finally, the product is detected visually or with a microtiter plate reader. The intensity of signal generated is proportional to the amount of initial analyte in the test mixture.

In a variation of the solid-phase assay, an antigen may be indirectly immobilized or captured, e.g. using an immobilized capture antibody which recognizes an irrelevant domain on the antigen or by using an antibody or other ligand which binds a "tag" engineered into the target protein, e.g. a polyhistidine sequence.

An alternate method of measuring binding of antibodies against surface antigens is by using whole cells that express (naturally or through genetic engineering) an antigen on the cell surface. The cells are incubated with a test solution containing the primary antibody. The unbound antibody is washed away and the cells are then incubated with an enzyme conjugated to antibodies specific for the primary antibody. Unbound enzyme conjugate is washed away and substrate solution added. The level of bound primary antibody is proportional to the amount of substrate hydrolysis. This will be quantitative if the number of cells per unit volume is held constant. Alternatively, detection be made using a radio-labeled ligand through direct binding or competition as described above. Protocols for ELISA assays are found in e.g. In: Ausebel, F M et al. *Current Protocols in Molecular Biology.* 2003 John Wiley & Sons, Inc.

Binding rates, association rates and dissociation rates, can also be measured using BIAcore technology which uses a solid phase binder or ligand and a mobile solution phase binder or ligand detected by plasmon surface resonance.

Methods for Assessing Effector Function

The role of antibody glycosylation in the clearance, and therefore pharmacokinetics of therapeutic Fc containing proteins seems minimal; binding to the neonatal Fc receptor (FcRn) thought responsible for IgG removal from circulation, appears unperturbed by a lack of N-linked oligosaccharide on the Fc portion of an antibody.

The IgG Fc receptors (FcR) that link IgG antibody-mediated immune responses with cellular effector functions include the Fc-gamma receptors: FcRI (CD64), FcRII (CD32) (both FcRIIA and FCRIIB), and FcRIII (CD16). All three are found displayed on monocytes. However, the elaboration of these receptors on various target cells appears to occur differentially and in response to other factors. Therefore, measurement of the affinity of glycosylation-modified Fc containing biotherapeutics for Fc-gamma receptors is one appropriate measurement for predicting enhanced effector functions.

Human IgG1 Abs with low levels of fucose in their Fc glycans have been reported to have greater affinity for human CD 16 FcR and dramatically enhanced in vitro activity in ADCC assays using human PBMC effector cells (Shinkawa et al. J Biol Chem 278(5):3466-3473, 2003; Shields et al. J Biol Chem 277(30):26733-26740, 2002; Umana et al., Nat Biotech 17:176-180, 1999).

A method of assessing effector functions using the in vitro ADCC assay can be performed in a quantitative manner. Thus, an in vitro assay can be designed to measure the ability of bound antibody to cause destruction of the cell displaying its cognate ligand by the correct selection of target and effector cell lines and assessing cell "kill" by either the inability of the cells to continue dividing or by release of internal contents, e.g. $^{51}Cr$ release. The target cell may be a cell line which normally expresses a target ligand for the antibody, antibody fragment, or fusion protein of the invention or may be engineered to express and retain the target protein on its surface. An example of such an engineered cell line is the K2 cell, an Sp2/0 mouse myeloma cell line that stably expresses on its surface recombinant human TNF that remains as a transmembrane form due to the introduction of a deletion of amino acids 1-12 of the mature cytokine (Perez et al., Cell 63:251-258, 1990). This cell line is useful for assessing alterations in ADCC activity of anti-TNF antibodies, antibody fragments, or engineered anti-TNFalpha targeting fusion proteins having Fc-domains or Fc-domain activity.

The effector cells for the in vitro ADCC activity assay may be PBMC (peripheral blood monocytic cells) of human or other mammal source. PBMC effector cells can be freshly isolated from after collecting blood from donors by approved methods. Other monocytic or macrophage cells which may be used are those derived from effusion fluids such as peritoneal exudates.

In vivo models for measuring the cellular immune functions are also available. For example, anti-CD3 antibodies can be used to measure T cell activation in mice, because T-cell activation is dependent on the manner in which the antibody Fc-domain engages specific Fcγ receptors. In vitro, the anti-tumor activity of a high fucose and a low fucose version of a chimeric human IgG1 Ab against CC chemokine receptor 4 were compared, no difference in their in vitro ADCC activity was observed (using mouse effector cells), however, the low fucose Ab showed more potent efficacy in vivo. No human effector cells were provided and the mice retain endogenous NK cells (Niwa et al. Cancer Res 64:2127-2133, 2004). As the CD 16 receptor on human NK cells has demonstrated enhanced sensitivity to fucose levels of IgG1 Abs, these data suggest that a mechanism distinct from what has been studied in human effector cells is operating in mice. One possibility is the more recently discovered mouse CD16-2 receptor (Mechetina et al. Immunogen 54:463-468, 2002). The extracellular domain of mouse CD16-2 has significantly higher sequence identity to human CD16A (65%) than does the better-known mouse CD16 receptor, suggesting that it may be more sensitive to fucose levels of IgGs that it binds than mouse CD 16. Its reported expression in mouse macrophage-like J774 cells is consistent with the possibility that mouse macrophages expressing CD16-2 may be responsible for the greater anti-tumor activity by the low fucose Ab described by Niwa et al. (2004). Thus, the study of Fc-receptor binding by human IgG1-type Fc containing proteins to murine effector cells is not predictive.

Protein Production Processes

Different processes involved with the production of Fc-containing proteins can impact Fc oligosaccharide structure, including sialic acid. In one embodiment, the host cells secreting the Fc-containing protein are cultured in the presence of serum, e.g., fetal bovine serum (FBS), that was not previously subjected to an elevated heat treatment (for example, 56° C. for 30 minutes). This can result in Fc-containing protein that contains no, or very low amounts of, sialic acid, due to the natural presence in the serum of active sialidase enzymes that can remove sialic acid from the Fc-containing proteins secreted from those cells. In another embodiment, the cells secreting the Fc-containing protein are cultured either in the presence of serum that was subjected to an elevated heat treatment, thereby inactivating sialidase enzymes, or in the absence of serum or other medium components that may contain sialidase enzymes, such that the Fc-containing protein has higher levels of sialic acid, for applications (e.g., therapeutic indications) when that might be desirable.

In another embodiment, the conditions used to purify and further process Fc-containing proteins are established that will favor optimal sialic acid content. For example, because sialic acid is acid-labile, prolonged exposure to a low pH environment, for example following elution from a protein A chromatography column or during viral inactivation processes, can simultaneously lead to a reduction in sialic acid content.

Host Cell Engineering

As described herein, the host cell chosen for expression of the recombinant Fe-containing protein or monoclonal antibody is an important contributor to the final composition, including, without limitation, the variation in composition of the oligosaccharide moieties decorating the protein in the immunoglobulin CH2 domain. Thus, one aspect of the invention involves the selection of appropriate host cells for use and/or development of a production cell expressing the desired therapeutic protein.

In one embodiment, the host cell is a cell which is naturally deficient or devoid of sialyltransferases. In another embodiment, the host cell is genetically modified or treated so as to be devoid of sialyltransferases. In a further embodiment, the host cell is a derivative host cell line selected to express reduced or undetectable levels of sialyltransferases. In yet another embodiment, the host cell is naturally devoid of, or is genetically modified or treated so as to be devoid of, CMP-sialic acid synthetase, the enzyme that catalyzes the formation of CMP-sialic acid, which is the source of sialic acid used by sialyltransferase to transfer sialic acid to the antibody. In a related embodiment, the host cell may be naturally devoid of, or is genetically modified or treated so as to be devoid of, pyruvic acid synthetase, the enzyme that forms sialic acid from pyruvic acid.

In an additional embodiment, the host cell may be naturally devoid of, or is genetically modified or treated so as to be devoid of, galactosyltransferases, such that antibodies expressed in said cells lack galactose. Without galactose, sialic acid will not be attached. In a separate embodiment, the host cell may naturally overexpress, or be genetically modified to overexpress, a sialidase enzyme that removes sialic acid from antibodies during production. Such a sialidase enzyme may act intracellularly on antibodies before the antibodies are secreted or be secreted into the culture medium and act on antibodies that have already been secreted into the medium. Methods of selecting cell lines with altered glycosylases and which express glycoproteins with altered carbohydrate compositions have been described (Ripka and Stanley, 1986. Somatic Cell Mol Gen 12:51-62; US2004/0132140). Methods of engineering host cells to produce antibodies with altered glycosylation patterns resulting in enhanced ADCC have been taught in e.g. U.S. Pat. No. 6,602,864, wherein the host cells harbor a nucleic acid encoding at least one glycoprotein modifying glycosyl transferase, specifically β (1,4)-N-acetylglucosamnyltranferase III (GnTIII).

Other approaches to genetically engineering the glycosylation properties of a host cell through manipulation of the host cell glycosyltransferase involve eliminating or suppressing the activity, as taught in EP1,176,195, specifically, alpha1,6 fucosyltransferase (FUT8 gene product). It would be obvious to one skilled in the art to practice the methods of host cell engineering in other than the specific examples cited above. Further, the engineered host cell may be of mammalian origin or may be selected from myeloma, lymphoma, yeast, insect or plant cells, or any derivative, immortalized or transformed cell thereof.

In another embodiment, the method of suppressing or eliminating the activity of the enzyme required for sialic acid attachment may be selected from the group consisting of gene silencing, such as by the use of siRNA, genetic knock-out, or addition of an enzyme inhibitor, such as by co-expression of an intracellular Ab or peptide specific for the enzyme that binds and blocks its enzymatic activity, and other known genetic engineering techniques. In another embodiment, a method of enhancing the expression or activity of an enzyme that blocks sialic acid attachment, or a sialidase enzyme that removes sialic acids that are already attached, may be selected from the group consisting of transfections with recombinant enzyme genes, transfections of transcription factors that enhance enzyme RNA synthesis, or genetic modifications that enhance stability of enzyme RNA, all leading to enhanced activity of enzymes, such as sialidases, that result in lower levels of sialic acid in the purified product. In another embodiment, specific enzyme inhibitors may be added to the cell culture medium.

Antibodies

An antibody described in this application can include or be derived from any mammal, such as but not limited to, a human, a mouse, a rabbit, a rat, a rodent, a primate, or any combination thereof and includes isolated human, primate, rodent, mammalian, chimeric, humanized and/or CDR-grafted anti-integrin antibodies, immunoglobulins, cleavage products and other specified portions and variants thereof. The invention also relates to antibody encoding or complementary nucleic acids, vectors, host cells, compositions, formulations, devices, transgenic animals, transgenic plants, and methods of making and using thereof, as described herein together as combined with what is known in the art.

The present invention further provides cells, cell lines, and cell cultures that express an immunoglobulin or fragment thereof capable of glycosylation in a CH2-domain which binds an antigen, a cytokine, an integrin, an antibody, a growth factor, a surface antigen which is a marker of cell lineage and differentiation, a hormone, a receptor or fusion protein thereof, a blood protein, a protein involved in coagulation, any fragment thereof, and any structural or functional analog of any of the foregoing. In a preferred embodiment, the immunoglobulin, fragment or derivative thereof binds an antigen on the surface of a target cell. In a particularly preferred embodiment the target cell is a tumor cell, a cell of the tumor vasculature, or an immune cell. In a specific embodiment, the immunoglobulin, fragment or derivative thereof binds to TNF, an integrin, a B-cell antigen, or tissue factor.

In yet another embodiment, the cells, cell lines, and cell cultures of the present invention may detectably express a fusion protein comprising a growth factor or hormone. Examples of the growth factors contemplated by the present invention include, but are not limited to, a human growth factor, a platelet derived growth factor, an epidermal growth factor, a fibroblast growth factor, a nerve growth factor, a human chorionic gonadotropin, an erythropoeitin, a thrombopoeitin, a bone morphogenic protein, a transforming growth factor, an insulin-like growth factor, or a glucagon-like peptide, and any structural or functional analog thereof.

Isolated antibodies of the invention include those having antibody isotypes with ADCC activity, especially human IgG1, (e.g., IgG1kappa and IgG1lamda), and, less preferred are IgG2 and IgG3, or hybrid isotypes containing altered residues at specific residues in the Fc domains are their counterparts from other species. The antibodies can be full-length antibodies (e.g., IgG1) or can include only an antigen-binding portion and an Fc portion or domain capable of eliciting effector functions including ADCC, complement activation, and C1q binding.

Furthermore, the immunoglobulin fragment produced by the cells, cell lines, and cell cultures of the present invention may include, but is not limited to Fc or other CH2 domain containing structures and any structural or functional analog thereof. In one embodiment, the immunoglobulin fragment is a dimeric receptor domain fusion polypeptide. In a specific embodiment, the dimeric receptor domain fusion polypeptide is etanercept. Etanercept is a recombinant, soluble TNFα receptor molecule that is administered subcutaneously and binds to TNFα in the patient's serum, rendering it biologically inactive. Etanercept is a dimeric fusion protein consisting of the extracellular ligand-binding portion of the human 75 kilodalton (p75) tumor necrosis factor receptor (TNFR) linked to the Fc portion of human IgG1. The Fc component of etanercept contains the CH2 domain, the CH3 domain and hinge region, but not the CH1 domain of IgG1.

Other products amenable to manufacture using the cell lines of the invention include therapeutic or prophylactic proteins currently manufactured by other types of animal cell lines and having a CH2 capable of being glycosylated. Particularly preferred are those therapeutic, glycosylated, CH2-domain containing proteins which bind to target antigens on a cell surface, which cell type it is desirable to incapacitate or eliminate from the body. A number of such therapeutic antibodies are engineered to contain the human IgG1, especially the IgG1, heavy chain which comprises a human CH1, CH2, and CH3 domain. Such therapeutic proteins include, but are not limited to those described herein below.

Infliximab now sold as REMICADE®. Infliximab is a chimeric IgG1κ monoclonal antibody with an approximate molecular weight of 149,100 daltons. It is comprised of human constant and murine variable regions. Infliximab binds specifically to human tumor necrosis factor alpha (TNF (alpha)) with an association constant of $10^{10}$ M-1. Infliximab neutralizes the biological activity of TNF(alpha) by binding with high affinity to the soluble and transmembrane forms of TNF(alpha) and inhibits binding of TNF(alpha) with its receptors. Cells expressing transmembrane TNF(alpha) bound by infliximab can be lysed in vitro or in vivo. Infliximab is indicated for the treatment of rheumatoid arthritis, Crohn's disease, and alkylosing spondylitis. Infliximab is given as doses of 3 to 5 mg/kg given as an intravenous infusion followed with additional similar doses at 2, 6, and/or 8 weeks thereafter and at intervals of every 8 weeks depending on the disease to be treated.

Daclizumab (sold as ZENAPAX®) is an immunosuppressive, humanized IgG1 monoclonal antibody produced by recombinant DNA technology that binds specifically to the alpha subunit (p55 alpha, CD25, or Tac subunit) of the human high-affinity interleukin-2 (IL-2) receptor that is expressed on the surface of activated lymphocytes. Daclizumab is a complementarity-determining regions (CDR) grafted mouse-human chimeric antibody. The human sequences were derived from the constant domains of human IgG1 and the variable framework regions of the Eu myeloma antibody. The murine sequences were derived from the CDRs of a murine anti-Tac antibody. Daclizumab is indicated for the prophylaxis of acute organ rejection in patients receiving renal transplants and is generally used as part of an immunosuppressive regimen that includes cyclosporine and corticosteroids.

Basiliximab (sold as SIMULECT®) is a chimeric (murine/human) monoclonal antibody produced by recombinant DNA technology, that functions as an immunosuppressive agent, specifically binding to and blocking the interleukin-2 receptor (alpha)-chain (IL-2R(alpha), also known as CD25 antigen) on the surface of activated T-lymphocytes. Based on the amino acid sequence, the calculated molecular weight of the protein is 144 kilodaltons. It is a glycoprotein obtained from fermentation of an established mouse myeloma cell line genetically engineered to express plasmids containing the human heavy and light chain constant region genes (IgG 1) and mouse heavy and light chain variable region genes encoding the RFT5 antibody that binds selectively to the IL-2R (alpha). Basiliximab is indicated for the prophylaxis of acute organ rejection in patients receiving renal transplantation when used as part of an immunosuppressive regimen that includes cyclosporine and corticosteroids.

Adalimumab (sold as HUMIRA®) is a recombinant human IgG1 monoclonal antibody specific for human tumor necrosis factor (TNF). Adalimumab was created using phage display technology resulting in an antibody with human derived heavy and light chain variable regions and human IgG1 kappa constant regions. HUMIRA® is indicated for reducing signs and symptoms and inhibiting the progression of structural damage in adult patients with moderately to severely active rheumatoid arthritis who have had an inadequate response to one or more DMARDs. HUMIRA® can be used alone or in combination with MTX or other DMARDs.

Rituximab (sold as RITUXAN®) is a genetically engineered chimeric murine/human monoclonal antibody directed against the CD20 antigen found on the surface of normal and malignant B lymphocytes. The antibody is an IgG1 kappa immunoglobulin containing murine light- and heavy-chain variable region sequences and human constant region sequences. Rituximab has a binding affinity for the CD20 antigen of approximately 8.0 nM. Rituximab is indicated for the treatment of patients with relapsed or refractory, low-grade or follicular, CD20-positive, B-cell non-Hodgkin's lymphoma. RITUXAN® is given at 375 mg/m 2 IV infusion once weekly for 4 or 8 doses.

Trastuzumab (sold as HERCEPTIN®) is a recombinant DNA-derived humanized monoclonal antibody that selectively binds with high affinity in a cell-based assay (Kd=5 nM) to the extracellular domain of the human epidermal growth factor receptor 2 protein, HER2. The antibody is an IgG 1 kappa that contains human framework regions with the complementarity-determining regions of a murine antibody (4D5) that binds to HER2. HERCEPTIN is indicated as single agent therapy for the treatment of patients with metastatic breast cancer whose tumors overexpress the HER2 protein and who have received one or more chemotherapy regimens for their metastatic disease. HERCEPTIN® in combination with paclitaxel is indicated for treatment of patients with metastatic breast cancer whose tumors overexpress the HER2 protein and who have not received chemotherapy for their metastatic disease. The recommended dosage is an initial loading dose of 4 mg/kg trastuzumab administered as a 90-minute infusion and a weekly maintenance dose of 2 mg/kg trastuzumab which can be administered as a 30-minute infusion if the initial loading dose was well tolerated.

Alemtuzumab (sold as CAMPATH®) is a recombinant DNA-derived humanized monoclonal antibody (Campath-1H) that is directed against the 21-28 kD cell surface glycoprotein, CD52. Alemtuzumab binds to CD52, a non-modulating antigen that is present on the surface of essentially all B and T lymphocytes, a majority of monocytes, macrophages, and NK cells, a subpopulation of granulocytes, and tissues of the male reproductive system. The Campath-1H antibody is an IgG1 kappa with human variable framework and constant regions, and complementarity-determining regions from a murine (rat) monoclonal antibody (Campath-1G). Campath is indicated for the treatment of B-cell chronic lymphocytic leukemia (B-CLL) in patients who have been treated with alkylating agents and who have failed fludarabine therapy. Determination of the effectiveness of Campath is based on overall response rates. Campath is given initially at 3 mg administered as a 2 hour IV infusion daily; once tolerated the daily dose should be escalated to 10 mg and continued until tolerated. Once this dose level is tolerated, the maintenance dose of Campath 30 mg may be initiated and administered three times per week for up to 12 weeks. In most patients, escalation to 30 mg can be accomplished in 3-7 days.

Omalizumab (sold as XOLAIR®) is a recombinant humanized IgG1(kappa) monoclonal antibody that selectively binds to human immunoglobulin E (IgE). Omalizumab inhibits the binding of IgE to the high-affinity IgE receptor (Fc(epsilon)RI) on the surface of mast cells and basophils. Reduction in surface-bound IgE on Fc(epsilon)RI-bearing cells limits the degree of release of mediators of the allergic response. Treatment with omalizumab also reduces the number of Fc(epsilon)RI receptors on basophils in atopic patients. Omalizumab is indicated for adults and adolescents (12 years of age and above) with moderate to severe persistent asthma who have a positive skin test or in vitro reactivity to a perennial aeroallergen and whose symptoms are inadequately controlled with inhaled corticosteroids. Omalizumab is administered SC every 2 or 4 weeks at a dose of 150 to 375 mg.

Efalizumab (RAPTIVA®) is an immunosuppressive recombinant humanized IgG1 kappa isotype monoclonal antibody that binds to human CD11a. Efalizumab binds to CD11a, the (alpha) subunit of leukocyte function antigen-1 (LFA-1), which is expressed on all leukocytes, and decreases cell surface expression of CD11a. Efalizumab inhibits the binding of LFA-1 to intercellular adhesion molecule-1 (ICAM-1), thereby inhibiting the adhesion of leukocytes to other cell types. Interaction between LFA-1 and ICAM-1 contributes to the initiation and maintenance of multiple processes, including activation of T lymphocytes, adhesion of T lymphocytes to endothelial cells, and migration of T lymphocytes to sites of inflammation including psoriatic skin. Lymphocyte activation and trafficking to skin play a role in the pathophysiology of chronic plaque psoriasis. In psoriatic skin, ICAM-1 cell surface expression is upregulated on endothelium and keratinocytes. CD11a is also expressed on the surface of B lymphocytes, monocytes, neutrophils, natural killer cells, and other leukocytes. Therefore, the potential exists for efalizumab to affect the activation, adhesion, migration, and numbers of cells other than T lymphocytes. The recommended dose of RAPTIVA® is a single 0.7 mg/kg SC conditioning dose followed by weekly SC doses of 1 mg/kg (maximum single dose not to exceed a total of 200 mg).

In another embodiment, a cell line of the invention is stably transfected or otherwise engineered to express a non-immunoglobulin derived polypeptide but which falls within the definition of an Fc-containing protein.

The nucleic acids encoding the antibodies and proteins of this invention can be derived in several ways well known in the art. In one aspect, the antibodies are conveniently obtained from hybridomas prepared by immunizing a mouse with the peptides of the invention. The antibodies can thus be obtained using any of the hybridoma techniques well known in the art, see, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

In another convenient method of deriving the target binding portion of the antibody, typically the variable heavy and/or variable light domains of an antibody, these portions are selected from a library of such binding domains created in, e.g., a phage library. A phage library can be created by inserting a library of random oligonucleotides or a library of polynucleotides containing sequences of interest, such as from the B-cells of an immunized animal or human (Smith, G. P. 1985. Science 228: 1315-1317). Antibody phage libraries contain heavy (H) and light (L) chain variable region pairs in one phage allowing the expression of single-chain Fv fragments or Fab fragments (Hoogenboom, et al. 2000, Immunol. Today 21(8) 371-8). The diversity of a phagemid library can be manipulated to increase and/or alter the immunospecificities of the monoclonal antibodies of the library to produce and subsequently identify additional, desirable, human monoclonal antibodies. For example, the heavy (H) chain and light (L) chain immunoglobulin molecule encoding genes can be randomly mixed (shuffled) to create new HL pairs in an assembled immunoglobulin molecule. Additionally, either or both the H and L chain encoding genes can be mutagenized in a complementarity determining region (CDR) of the variable region of the immunoglobulin polypeptide, and subsequently screened for desirable affinity and neutralization capabilities. Antibody libraries also can be created synthetically by selecting one or more human framework sequences and introducing collections of CDR cassettes derived from human antibody repertoires or through designed variation (Kretzschmar and von Ruden 2000, Current Opinion in Biotechnology, 13:598-602). The positions of diversity are not limited to CDRs but can also include the framework segments of the variable regions or may include other than antibody variable regions, such as peptides.

Other libraries of target binding components which may include other than antibody variable regions are ribosome display, yeast display, and bacterial displays. Ribosome display is a method of translating mRNAs into their cognate proteins while keeping the protein attached to the RNA. The nucleic acid coding sequence is recovered by RT-PCR (Mattheakis, L. C. et al. 1994. Proc. Natl. Acad. Sci. USA 91, 9022). Yeast display is based on the construction of fusion proteins of the membrane-associated alpha-agglutinin yeast adhesion receptor, aga1 and aga2, a part of the mating type system (Broder, et al. 1997. Nature Biotechnology, 15:553-7). Bacterial display is based on fusion of the target to exported bacterial proteins that associate with the cell membrane or cell wall (Chen and Georgiou 2002. Biotechnol Bioeng, 79:496-503).

In comparison to hybridoma technology, phage and other antibody display methods afford the opportunity to manipulate selection against the antigen target in vitro and without the limitation of the possibility of host effects on the antigen or vice versa.

Host Cells

The host cells described herein comprise host cells capable of producing specific antibodies with defined sialic acid content in the oligosaccharide content of said antibodies.

Unlike most genes that are transcribed from continuous genomic DNA sequences, antibody genes are assembled from gene segments that may be widely separated in the germ line. In particular, heavy chain genes are formed by recombination of three genomic segments encoding the variable (V), diversity (D) and joining (J)/constant (C) regions of the antibody. Functional light chain genes are formed by joining two gene segments; one encodes the V region and the other encodes the J/C region. Both the heavy chain and kappa light chain loci contain many V gene segments (estimates vary between 100 s and 1000 s) estimated to span well over 1000 kb. The lambda locus is, by contrast, much smaller and has been shown to span approximately 300 kb on chromosome 16 in the mouse. It consists of two variable gene segments and four joining/constant (J/C) region gene segments. Formation of a functional gene requires recombination between a V and a J/C element.

In the B-cell in which the antibody is naturally produced, control of transcription of both rearranged heavy and kappa light chain genes depends both on the activity of a tissue specific promoter upstream of the V region and a tissue specific enhancer located in the J-C intron. These elements act synergistically. Also, a second B-cell specific enhancer has been identified in the kappa light chain locus. This further enhancer is located 9 kb downstream of $C_{kappa}$. Thus, the hybridoma method of immortalizing antibody expression genes relies on the endogenous promoter and enhancer sequences of the parent B-cell lineage. Alternatively, nucleic acids of the present invention can be expressed in a host cell by turning on (by manipulation) in a host cell that contains endogenous DNA encoding an antibody of the present invention. Such methods are well known in the art, e.g., as described in U.S. Pat. Nos. 5,580,734, 5,641,670, 5,733,746, and 5,733,761, entirely incorporated herein by reference.

Cloning of antibody genomic DNA into an artificial vector is another method of creating host cells capable of expressing antibodies. However, expression of monoclonal antibodies behind a strong promoter increases the chances of identifying high-producing cell lines and obtaining higher yields of monoclonal antibodies. Antibodies of the invention can be produced in a host cell transfectoma using, for example, a combination of recombinant DNA techniques and gene transfection methods as is well known in the art (e.g., Morrison, S. (1985) Science 229:1202).

Systems for cloning and expression of a polypeptide in a variety of different host cells are well known. Suitable host cells include bacteria, mammalian cells, plant cells, yeast and baculovirus systems and transgenic plants and animals. Mammalian cell lines available in the art for expression of a heterologous polypeptide intact glycosylated proteins include Chinese hamster ovary (CHO) cells, HeLa cells, baby hamster kidney cells (BHK), NSO mouse melanoma cells and derived cell lines, e.g. SP2/0, YB2/0 (ATC CRL-1662) rat myeloma cells, human embryonic kidney cells (HEK), human embryonic retina cells PerC.6 cells, hep G2 cells, BSC-1 (e.g., ATCC CRL-26) and many others available from, for example, American Type Culture Collection, Manassas, Va. (www.atcc.org). A common, preferred bacterial host is *E. coli*.

Mammalian cells such as CHO cells, myeloma cells, HEK293 cells, BHK cells (BHK21, ATCC CRL-10), mouse Ltk-cells, and NIH3T3 cells have been frequently used for stable expression of heterologous genes. Cell lines such as Cos (COS-1 ATCC CRL 1650; COS-7, ATCC CRL-1651) and HEK293 are routinely used for transient expression of recombinant proteins.

Preferred mammalian host cells for expressing the recombinant antibodies of the invention include myeloma cells such as Sp2/0, YB2/0 (ATC CRL-1662), NSO, and P3X63.Ag8.653 (e.g. SP2/0-Ag14) because of their high rate of expression. In particular, for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

CHO-K1 and DHFR-CHO cells DG44 and DUK-B11 (G. Urlaub, L. A. Chasin, 1980. Proc. Natl. Acad. Sci. U.S.A. 77, 4216-4220) are used for high-level protein production because the amplification of genes of interest is enabled by the incorporation of a selectable, amplifiable marker, DHFR using e.g. the drug methotrexate (MTX) (R. J. Kaufman, 1990. Methods Enzymol. 185: 537-566). DHFR⁻ CHO cells can be successfully used to produce recombinant mAbs at a high level. DHFR⁻ CHO may produce ant-MCP-1 antibodies at the rate of 80-110 mg $10^6$ cells$^{-1}$ day$^{-1}$ or more than 200 mg $10^6$ cells$^{-1}$ day$^{-1}$. A variety of promoters have been used to obtain expression of H- and L-chains in these CHO cells, for example, the b-actin promoter, the human CMV MIE promoter, the Ad virus major late promoter (MLP), the RSV promoter, and a murine leukemia virus LTR. A number of vectors for mAb expression are described in the literature in which the two Ig chains are carried by two different plasmids with an independent selectable/amplifiable marker. Vectors containing one antibody chain, e.g. the H-chain, linked to a DHFR marker, and an L-chain expression cassette with the Neo$^r$ marker or vice versa to can be used obtain up to180 mg of a humanized mAb L$^{-1}$ 7 day$^{-1}$ in spinner flasks. The methods used for initial selection and subsequent amplification can be varied and are well known to those skilled in the art. In general, high-level mAb expression can be obtained using the following steps: initial selection and subsequent amplification of candidate clones, coselection (e.g., in cases where both H-chain and L-chain expression vectors carry DHFR expression unit) and amplification, coamplification using different amplifiable markers, and initial selection and amplification in mass culture, followed by dilution cloning to identify individual high-expressing clones. Because integration sites may influence the efficiency of H-chain and L-chain expression and overall mAb expression, single vectors have been created in which the two Ig-chain expression units are placed in tandem. These vectors also carry a dominant selectable marker such as Neo$^r$ and the DHFR expression cassette. For a review see Ganguly, S. and A. Shatzman. Expression Systems, mammalian cells IN: Encyclopedia of Bioprocess Technology: Fermentation, Biocatalysis, and Bioseparation. 1999 by John Wiley & Sons, Inc.

Cockett et al. (1990. Bio/Technology 8, 662-667) developed the GS system for high-level expression of heterologous genes in CHO cells. Transfection of an expression vector containing a cDNA (under the transcriptional control of the hCMV promoter) and a GS mini gene (under the control of the SV40 late promoter) into CHO-K1 cells (followed by selection with 20 mM to 500 mM MSX) can be used to yield clones expressing the antibodies of the invention in yields comparable to that of the DHFR-CHO systems. The GS system is discussed in whole or part in connection with European Patent Nos. 0 216 846, 0 256 055, and 0 323 997 and European Patent Application No. 89303964.4.

While having described the invention in general terms, the embodiments of the invention will be further disclosed in the following examples.

Example 1

Exymatic Modification of Galactosylation and Sialylation of Antibodies

To galactosylate purified antibody samples via enzymatic method, bovine β-1,4-galactosyltransferase (β1,4GT) and UDP-Gal obtained from Sigma Chemical Co. (St. Louis, Mo.) are added to the antibody samples. Recombinant rat liver α-2,3-sialyltransferase (α2,3ST), recombinant α-1,3- galactosyltransferase (α1,3GT) and CMP-Sia were obtained from Calbiochem (San Diego, Calif.). PNGase F was obtained from New England Biolabs (Beverly, Mass.) or from Prozyme (San Leandro, Calif.) or from Selectin BioSciences (Pleasant Hill, Calif.). β-Galactosidase and β-glucosaminidase from *Diplococcus pneumoniae* were obtained from either ProZyme or from Selectin BioSciences. β-Galactosidase from bovine kidney and all other enzymes were either from ProZyme or from Selectin BioSciences. NAP-5 and HiTrap protein A columns were from Pharmacia Biotech (Piscataway, N.J.). All other reagents were of analytical grade.

An enzymatically deglycosylated form (termed Gno) of Ab1 was prepared to serve as a control antibody that lacks Fc immune effector function. This variant was prepared by taking Ab1 (~10 mg in 1.0 mL of buffer) in 100 mM MES buffer (pH 7.0) and treating it with 1000 U of PNGase F at 37° C. for 24 hours. Another aliquot of enzyme was added and the incubation was continued for an additional 24 hours. The deglycosylated Ab1 was purified using a HiTrap Protein A column and formulated into PBS, pH 7.0. The Gno glycoform was characterized by MALDI-TOF-MS to confirm the deglycosylation.

In addition to the laboratory-manipulated Ab preparations, Ab sublots naturally differing in sialic acid content, referred to here as 'natural variants,' were also compared. The unmodified antibody was termed Ab1 PBS after material from the original lot was buffer-exchanged into PBS. Human IgG1 monoclonal Abs, Ab1 and Ab3, in which members of a pair differed in the extent of Fc sialylation, apparently due to the different production processes used to prepare them (but produced by the same host cell type). The Ab1 variants, Ab1-20 and Ab1-29, contained 20% and 29% sialylated glycans, respectively, and Ab5 variants, Ab5-20 and Ab5-26, contained 0% and 26% sialylated glycans, respectively. Otherwise, members of each pair had the same amino acid sequences, the same levels of Fc fucosylation and bisecting GlcNAc content (MALDI-TOF mass spectrometry analyses), and the same low level of Ab aggregates (<1% by SEC-HPLC analyses).

A summary of Ab and Fc-containing protein preparations used in the various bioassays and the manner in which they were derived is summarized in Table 1.

TABLE 1

Summary list of test Fc-containing proteins preparations used herein

Figure 6:
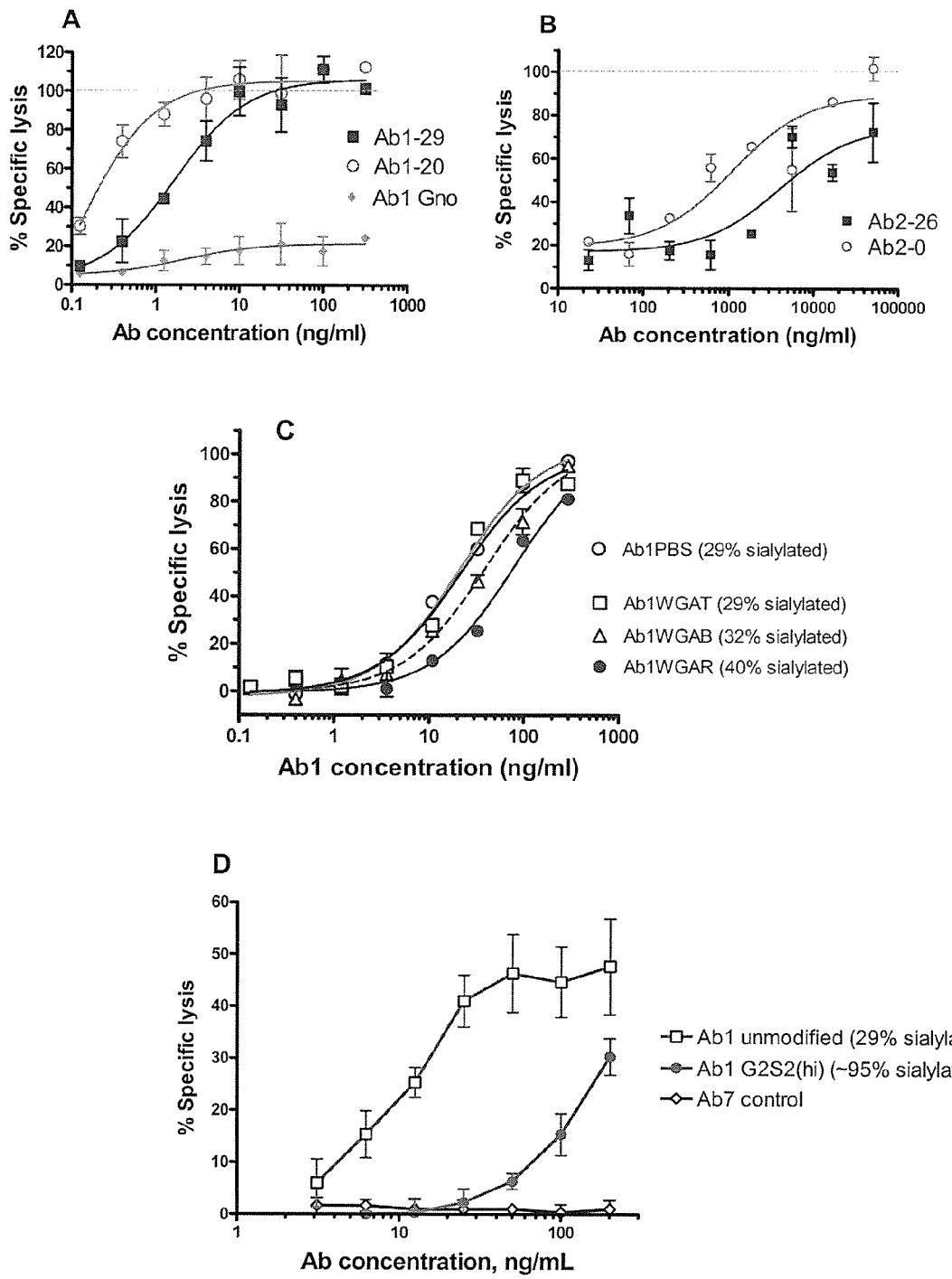
FIGS. 6A-D are graphs showing results of in vitro ADCC assays performed using Ab1 that differ in sialic acid content, K2 target cells that overexpress TNF on their cell surface, and human PBMC effector cells that express FcγRs. (A) Ab1 natural glycosylation variants, (B) Ab2 natural glycosylation variants, (C) Comparison of three sublots of Ab1 that differ in sialic acid content following WGA lectin affinity-based fractionation, and enzymatically deglycosylated (Gno) Ab1, (D) Comparison of an untreated Ab1 sample and a fully sialylated Ab1 G2S2 sample, or Ab7 isotype-matched negative control Ab. Samples were analyzed in triplicate (error bars represent s.d.) and the results shown are representative of three independent experiments for each pair of variants. The difference in activity between these test samples was significant ($P<0.0001$ for graphs A, C, and D; $P=0.0016$ for graph B) as determined by extra sum of squares F-test.
Figure 8:
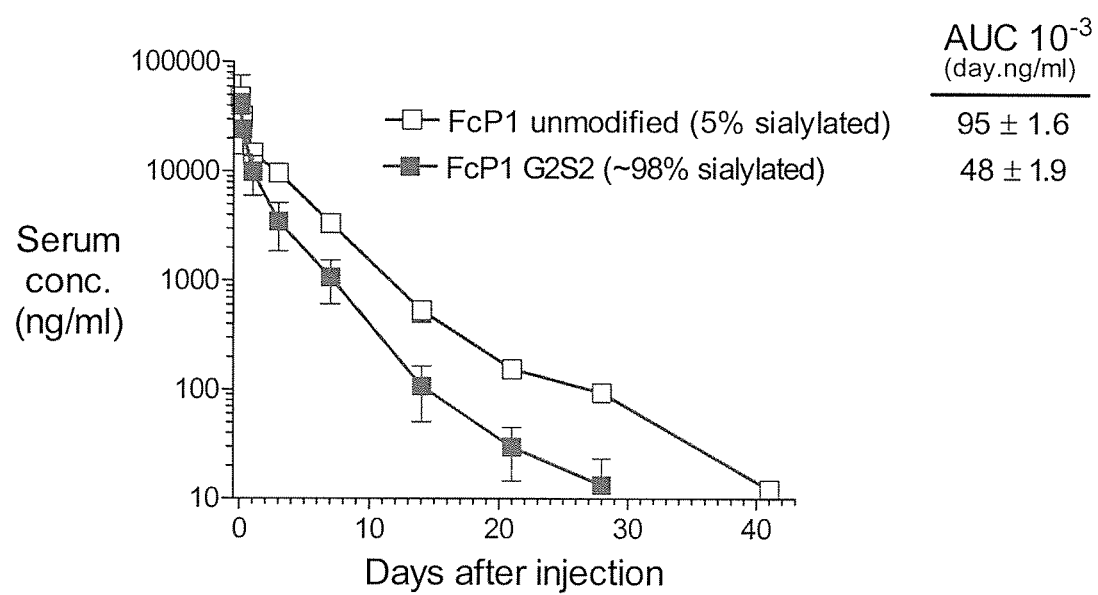
FIG. 8 is a graph showing the relationship between time after administration and serum concentration of the Fc-portion of a fusion protein (FcP 1) which had been fully sialylated (G2S2) or unmodified.

| Parent antibody | Specific variant | % sialylation | Description |
|---|---|---|---|
| Ab1 | — | — | anti-TNF human IgG1 antibody |
| | Ab1 unmodified, Ab1-29 | 29 | in original formulation, natural sialic acid variant |
| | Ab1 Gno | N.A. | enzymatically deglycosylated |
| | Ab1PBS | 29 | unmodified, buffer-exchanged into PBS |
| | Ab1-20 | 20 | natural sialic acid variant |
| | Ab1MAAB | 43 | bound to MAA lectin column |
| | Ab1WGAB | 32 | bound to WGA lectin column |
| | Ab1WGAR | 40 | retarded by WGA lectin column |
| | Ab1WGAT | 29 | passed through WGA lectin column |
| | Ab1-WGAR-41 | 41 | retarded by WGA lectin column |
| | Ab1-WGAT-29 | 29 | passed through WGA lectin column |
| | Ab1 G2 | 0 | enzymatically modified to full galactosylation |
| | Ab1 G2S2(hi) | 95 | enzymatically modified to G2S2 |
| | Ab1 G2S2(lo) | 33 | G2S2 that lost most of the sialic acid |
| Ab 2 | — | — | anti-TNF human IgG1 antibody |
| | Ab2 unmodified | 5% | unmodified used in FcγRI binding, FIG. 6 |
| | Ab2 G2 | 0% | modified; used in mouse PK study, FIG. 8 |
| | Ab2 G2S2 | ~90% | modified; used in mouse PK study, FIG. 8 |
| | Ab2 AlaAla | not relevant | mutant anti-TNF that lacks affinity for FcγR |
| | Ab2 GT-WGAT | 5 | passed through WGA lectin column |
| | Ab2 GT-WGAR | 67 | galactosylated and bound to a WGA lectin column |
| Ab3 | — | — | specific for a cytokine subunit |
| | Ab3(lo) | 2 | natural sialic acid variant |
| | Ab3(hi) | 42 | natural sialic acid variant |
| Ab4 | Ab4 | — | mouse IgG1 (lacks affinity for human FcγRI) |
| Ab5 | Ab5 | | Binds heterodimeric cell surface receptor |
| | Ab5-0 | 0 | Natural glycosylation variant |
| | Ab5-26 | 26 | Natural glycosylation variant |
| FcP1 | — | — | Fc-containing, non-Ab protein |
| | FcP1 unmodified | 5 | unmodified, for PK, FIG. 8 |
| | FcP1 G2S2 | ~98 | modified to G2S2, for PK, FIG. 8 |

The test samples all contain human $IgG_1$ hinge, CH2, and CH3 domains. Ab1, Ab2, Ab3, and Ab5 are monoclonal IgG Abs with human IgG1 and kappa constant regions. Ab1 is a fully human Ab specific for human TNF and Ab2 is a mouse/human chimeric Ab specific for human TNF. Ab3 is a fully human Ab specific for one of the subunits of a heterodimeric proinflammatory cytokine. All four Abs were expressed in transfected Sp2/0 mouse myeloma cells. Ab5 is a fully human antibody directed to a subunit of a heterodimeric cell surface receptor. FcP1 is a dimeric fusion protein comprising the human the human IgG1 hinge, CH2 and CH3 domains.

G2 glycoforms were prepared by subjecting IgG samples in 100 mM MES buffer (pH 7.0) (~10 mg in 1.0 mL of buffer) to 50 milliunits of β1,4GT, 5 μmol of UDP-Gal, and 5 μmol of $MnCl_2$ at 37° C. for 24 hours. Another aliquot of enzyme and UDP-Gal was added and the mixture was incubated for an additional 24 hours at 37° C. The regalactosylated IgG samples were purified using a HiTrap protein A column. The oligosaccharides were released by PNGase F and characterized by MALDI-TOF-MS and by HPLC as described below.

The G2S2 glycoform was made by bringing IgG samples into 100 mM MES buffer (pH 7.0) (~10 mg in 1.0 mL of buffer) using NAP-5 columns according to the manufacturer's suggested protocol. To this solution were added 50 milliunits each of β1,4GT and α2,3ST and 5 μmol each of UDP-Gal, CMP-Sia (NANA isomer), and $MnCl_2$. The mixture was incubated at 37° C. After 24 hours, another aliquot of enzymes was added along with the nucleotide sugars and the mixture incubated for an additional 24 hours at 37° C. The G2S2 glycoform of IgG samples were purified as described above. For one particular Ab1 G2S2 lot, Ab1 G2S2(lo), the sialic acid that was originally attached was subsequently lost during storage, possibly due to a contaminating sialidase. Analyses showed that only 30% of the Fc oligosaccharides in Ab1 G2S2(lo) contained sialic acid, whereas ~95% of oligosaccharides in Ab1 G2S2(hi) contained sialic acid.

The glycan structures of the Ab preparations were analyzed by various methods. To perform MALDI-TOF-MS analysis of intact IgG Abs, IgG samples were brought into 10 mM Tris-HCl buffer, pH 7.0 and adjusted concentration to ~1 mg/mL buffer. About 2 μl of IgG solution was mixed with 2 μl of matrix solution (the matrix solution was prepared by dissolving 10 mg sinnapinic acid in 1.0 ml of 50% acetonitrile in water containing 0.1% trifluoroacetic acid) and 2 ml of this solution was loaded onto the target and allowed to air dry. MALDI-TOF-MS was acquired using a Voyager DE instrument from Applied BioSystems (Foster City, Calif.).

To perform MALDI-TOF-MS analysis of released Fc glycans, IgG samples (~50 μg), before and after in vitro glycosylation reactions, were digested with PNGase F in 10 mM Tris-HCl buffer (50 μl) pH 7.0 for 4 hours at 37° C. The digestion was stopped by acidifying the reaction mixture with 50% acetic acid (~5 μl) and then passed through a cation-exchange resin column as described previously (Papac et al., 1996; Papac et al., 1998; Raju et al., 2000). These samples containing a mixture of acidic and neutral oligosaccharides were analyzed by MALDI-TOF-MS in the positive and negative ion modes, as described elsewhere (Papac et al., 1996; Papac et al., 1998; Raju et al., 2000) using a Voyager DE instrument from Applied BioSystems (Foster City, Calif.).

HPLC analysis of Fc glycans was done by digesting IgG samples (~50 μg) in 10 mM Tris-HCl buffer (~50 μl) pH 7.0 with PNGase F at 37° C. for 4-8 hours. Derivatization of the released oligosaccharides with anthranilic acid (2-aminobenzoic acid) was carried out as described (see Anumula K R, Anal Biochem. 2000 Jul. 15;283(1):17-26). Briefly, a solution of 4% sodium acetate $3H_2O$ (w/v) and 2% boric acid (w/v) in methanol was prepared first. The derivatization reagent was then freshly prepared by dissolving ~30 mg of anthranilic acid (Aldrich) and ~20 mg of sodium cyanoborohydride (Aldrich) in 1.0 ml of methanol-sodium acetate-borate solution. IgG-derived oligosaccharides (<3 nmol in 20-50 μl of water) were mixed with 0.1 ml of the anthranilic acid (AA) reagent solution in 1.6 ml polypropylene screw cap freeze vials with 'O' rings (Sigma) and capped tightly. The vials were heated at 80° C. in an oven or heating block (Reacti-Therm, Pierce) for 1-2 hours. After cooling the vials to room temperature, the samples were diluted with water to bring the volume to ~0.5 ml. Derivatized oligosaccharides were purified by using NAP-5 columns.

Example 2

Binding to Low-Affinity Cellular FC Receptors

Of the several types of Fc-receptors on effector cells, $Fc_{gamma}$ types II and III are considered low or intermediate affinity receptors. Generally, monomeric binding may be of too low an affinity to be detected or at very low levels. For example, monomeric IgG binding to $Fc_{gamma}$ type IIA is more difficult to measure. These receptors function to bind immune complexes, which due to their multivalent nature bind more avidly, presumably due to a slow-off rate of the complex.

Human K562 cells, which express FcγRIIA as the only Fcγ receptor, were used in two types of binding assays to test whether variations in sialic acid content in the Fc glycan affect binding to this low-affinity human Fcγ receptor. To obtain sufficient avidity of binding to FcγRIIA, which has low affinity for monomeric IgG, immune complexes were prepared by mixing anti-TNF test Abs with homotrimeric TNF in a 2:1 molar ratio, a ratio that was shown to result in only trace amounts of free Ab or free TNF. The dependence on immune complexes was illustrated when radiolabeled Ab2 alone binding to the K562 cells was not detectable at concentrations up to 1 ug/ml but Ab2:TNF complexes showed significant binding at 0.02 ug/ml (data not shown).

Competition Binding Format.

Two sets of IgG immune complexes were prepared, a labeled complex containing the human IgG1 antibody with irrelevant specificity complexed to an anti-V region specific non-human Ab and Ab5. To create the labeled complex, a chimeric monoclonal Ab with hamster V regions with human IgG1 and light chain kappa constant regions was iodinated using IODO-GEN reagent as previously described (Knight et al., 1993). A rat IgG2a monoclonal Ab specific for the V region idiotype of the hamster-human chimera, was then mixed in a 1:1 molar ratio in PBS for 30 min to allow formation of radiolabeled immune complexes. The rat anti-Id was shown to not contribute to FcγRIIA binding directly as when complexes were made with the deglycosylated hamster-human chimera, little binding occurred; whereas, complexes with unmodified chimeric Ab showed high levels of binding (data not shown). In addition, there was no detectable cross-reactivity between the agents used to make the separate immune complexes which might indicate that one immune complex might bind to the other immune complex (data not shown).

For the test complexes, sialic acid variants of Ab1 were mixed with human TNF homotrimer at a 2:1 molar ratio (shown by light scattering analysis to result in the very little unbound Ab plus unbound TNF) in PBS at room temperature for 30 minutes. In one set of experiments, complexes of Ab1 natural variants with 20 and 29 percent sialic acid were compared to each other. In a second set of experiments, Ab1-29:TNF complex was compared to the lectin column enhanced preparation Ab1-43:TNF complex. In both cases, the control complex was Ab1-Gno:TNF where the antibody has been enzymatically stripped of glycan.

Human K562 cells were seeded at $3 \times 10^5$ cells/well in 96-well plates in IMDM, 5% FBS. A fixed amount of the radiolabeled antibody complex was added to varying amounts of the test antibody complex and the combined mix added to the K562 cells such that each well contained a final concentration of 0.1 μg/ml of iodinated antibody complex. The plates were incubated for 16-18 hours at 4° C., after which unbound Ab removed by washing 3 times with IMDM, 5% FBS, and the number of counts bound to the cells determined using a gamma counter.

Results.

Figure 4:
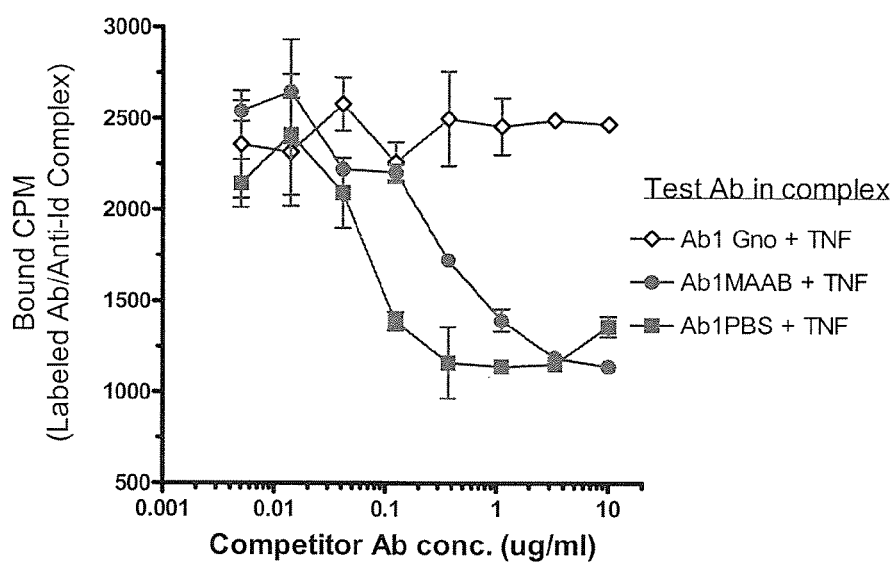
FIGS. 4A and 4B are graphs showing the binding of different Ab1:TNF immune complexes to human FcγRII on K562 cells by two different formats. (A) Competition binding measured by adding varying amounts of unlabeled complexes of Ab1 and TNF to the cells in the presence of a fixed amount of $^{125}$I-labeled human IgG1 Ab5 complexed with Ab6, a mouse monoclonal Ab specific for Ab5. (B) Direct binding measured by adding to the K562 cells varying amounts of Ab1 complexed with $^{125}$I-labeled TNF.
Figure 4:
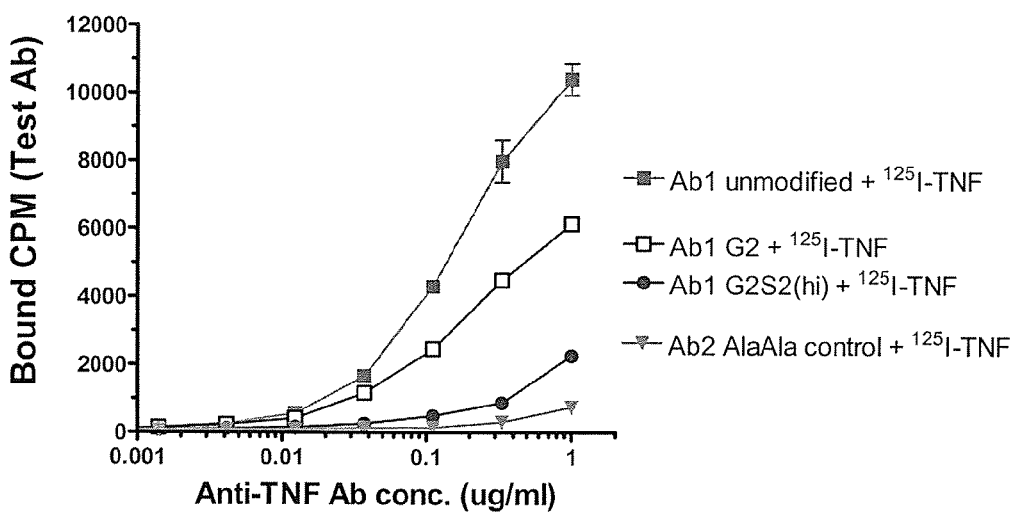

Increasing amounts of unlabeled competitor immune complexes increasingly inhibited binding by the radiolabeled immune complex. The sialic acid variants, unmodified Ab1 (29% sialylated) and Ab1 MAAB (43% sialylated) showed that the complex with the more highly sialylated Ab was required at 5 to 10-fold higher concentrations than the complex with the less sialylated Ab1 in order to produce the same extent of binding to FcγRII (FIG. 4A). For the natural variants of Ab1 differing by 9% sialic acid content (20 v 29), the difference was about 4-fold higher avidity for the less sialylated preparation (not shown). Thus, the presence of the NGNA isomer form of sialic acid, as a result of recombinant expression in a murine myeloma host cell, on this human IgG1 reduced the avidity of the immune complexes for human FcγRII.

Binding of Immune Complexes to the K562 Cells.

Ab1 test samples were mixed with $^{125}$I-labeled human TNF in a fixed 2:1 molar ratio, and then varying amounts of the resulting immune complex added to $3 \times 10^5$ K562 cells in a 96-well culture plate. A comparison of Ab1 G2:TNF complexes (non-sialylated Ab) vs Ab1 G2S2(hi):TNF complexes (fully sialylated Ab) showed that the fully sialylated Ab bound with much less avidity, with the highly sialylated variant being required at 10-fold higher concentrations than the asialylated variant to achieve the same degree of binding (FIG. 4B). These results indicate that the presence of the NANA isomer of sialic acid, introduced by in vitro enzymatic modifications, reduced the avidity of the antibody for human FcγRII which could be attributable to a reduction in binding affinity to the target (TNF), thereby causing the Ab:TNF complexes to be less stable, by reducing the affinity of the constant region for the Fc-receptor, or both.

Ab Binding to Cellular FcγRIIIa.

To analyze Ab binding to FcγRIIIa on natural killer cells (NK), human PBMCs were isolated as described above, and the NK cells were isolated from PBMCs by magnetic cell sorting using an NK Cell Isolation Kit (Miltenyi Biotec). NK cells were cultured overnight in 96-well plates at $1\times10^5$ cells per well in DMEM medium with 10% FBS at 37° C. with 5% $CO_2$. Anti-FcγRIIIa mAb 3G8[22] (BD Biosciences Pharmingen) was labeled with $^{125}$I using Iodogen tubes (Pierce) to a specific activity of 11 μCi/μg. The iodinated mAb 3G8 was pre-mixed with varying amounts of unlabeled competitor Ab in DMEM, 10% FBS and the Ab mixture added to the NK cells for a final concentration of 0.3 μg/ml iodinated 3G8. Cells were incubated at 4° C. for 16 hrs and then unbound IgG removed by washing 4 times with PBS. The number of CPMs bound to the cells was determined using a gamma counter.

U-937 cells (not pre-treated to enhance FcγR expression) that had been cultured in RPMI 1640 medium supplemented with 2 mM L-glutamine, 1 mM sodium pyruvate, and 10% FBS (U-937 medium) were seeded into 96-well plates to have $3\times10^5$ cells per well in 50 μl of U-937 medium. Ab2 (human IgG1) was labeled with $^{125}$I to a specific activity of 17 μCi/μg. The iodinated Ab2 Ab was pre-mixed with varying amounts of unlabeled competitor Ab2 samples in U-937 medium. 50 μl of the Ab mix was then added to the 50 μl of U-937 cells to have a final concentration of 0.2 μg/ml of iodinated Ab3 in all wells. Cells were incubated at 4° C. for 16 hrs and the unbound Ab was removed by washing three times with U-937 medium. The number of CPMs bound to the cells was determined using a gamma counter.

To test whether Ab variants show differential affinity for FcγRIIIa, freshly-isolated NK cells were isolated from healthy human donors and used in competition binding experiments involving radiolabeled mAb 3G8, an anti-FcγRIIIa Ab that competes for binding with Fc, and unlabeled Abs as competitors. Free, uncomplexed Abs were used instead of immune complexes (which generally show much greater binding to FcγRIIIa) so that the results would not be confounded by differences in stability of the soluble immune complexes themselves, which can be influenced by Fc sialic acid content (our unpublished data). The results showed that the higher sialylated natural variant of Ab1, Ab1-29, had a reduced affinity for FcγRIIIa on the NK cells, being required at 4-fold higher concentrations than Ab1-20 to achieve the same degree of binding (FIG. 5A). There was a similar difference with the natural variants of Ab5, where Ab5-26 was required at 5-fold higher concentrations than Ab5-0 to compete against mAb 3G8 to the same extent (FIG. 5B). Similar results were obtained in each experiment when using NK cells from at least two other blood donors (data not shown; FcγRIIIa allotype not determined). These results showed that higher levels of sialylation can reduce IgG affinity for FcγRIIIa and, therefore, almost certainly contributed to the observed reduction in ADCC activity.

When the same experiment was done with the pairs of variants derived by lectin fractionation, however, the higher sialylated variants were seen to bind FcγRIIIa just as well, and perhaps slightly better, than the less sialylated variants (FIGS. 5C and 5D). The reasons for the different results with the two pairs of natural variants and two pairs of lectin-derived variants is not known, but a good possibility is that there are differences in the locations of the sialic acid residues that are present.

Example 3

In Vitro ADCC Assays

The target cells for the anti-TNF Ab comprised an Sp2/0 mouse myeloma cell line that stably expresses on its surface recombinant human TNF that remains in a transmembrane form due to the introduction of a deletion of amino acids 1-12 of mature TNF (Perez et al., 1990). K2 cells were cultured in Iscove's media containing heat inactivated FBS, 2 mM L-glutamine, 1 mM sodium pyruvate, 0.1 mM non-essential amino acids, and MHX. Culture media and supplements were purchased from Gibco (Invitrogen). Cells were passaged 1:5 every 2-3 days. On the day of the assay, K2 cells were centrifuged and washed once with PBS. Cells were adjusted to about $1\times10^6$ cells/ml with the culture medium and 15 microliters of BATDA fluorescent labeling reagent (in Delfia EuTDA Cytotoxicity Reagent Kit, Perkin-Elmer Life Sciences) was added to 5 ml of cells (Blomberg et al., 1996). Cells were incubated for 30 minutes at 37° C., then washed twice with PBS at 1000 rpm, 5 min. Immediately prior to mixing with PBMC effector cells, targets cells were centrifuged and resuspended at $2\times10^5$ cells/ml in Iscove's media containing 1% BSA.

PBMC effector cells were isolated from healthy donors after collecting blood into heparinized vacutainers, and diluting two-fold with PBS. Thirty mls of diluted blood was layered on top of 15 ml of Ficoli-Paque (Amersham, Uppsala, Sweden) in a 50 ml conical tube and centrifuged at 1500 rpm, 30 min at room temperature (RT). The interface (buffy layer) containing PBMCs was collected and washed twice with PBS and centrifuged at 1200 rpm, 10 min, RT. Cells were resuspended in Iscove's media containing 5% heat inactivated FBS, 2 mM L-glutamine, 1 mM sodium pyruvate and 0.1 mM non-essential amino acids. PBMCs were activated for approximately 4 hours at 37° C., 5% $CO_2$ by incubating on 100 mm tissue culture dishes (Corning) that had been coated with OKT3 (10 ug/ml in PBS, Ortho Pharmaceutical) overnight at 4° C. and rinsed with PBS. PBMCs were collected, washed once with Iscove's media containing 1% BSA; counted and resuspended to approximately $1\times10^7$ cells/ml.

Ab1's test samples, including the negative control variant Ab1 Gno, were diluted serially in Iscove's—1% BSA media. Fifty microliters of target cells (~10,000) and 100 microliters of antibody were added to a round bottom 96 well plate (Corning). Fifty (50) microliters of effector cells (~500,000 cells) were added to the mixture, and the plate was centrifuged at 1000 rpm for 5 min, RT. The ratio of E:T was usually 50:1, however, 35:1 was sometimes used. For background fluorescence, wells were incubated with effector cells, target cells and media. For maximal fluorescence, 10 microliters of lysis solution (from Delfia EuTDA Cytotoxicity kit) was added to background wells. For the ADCC assay, cells were incubated at 37° C., 5% $CO_2$, for approximately 2 hours. 20 microliters of supernatant was transferred to a 96 well flat bottom plate (Corning). 200 microliters of Europium solution (Delfia EuTDA Cytotoxcity Kit) was added and the plate was put on a plate shaker for 10 minutes at RT. Fluorescence was measured in the time-resolved fluorometer, EnVision Instrument (Perkin-Elmer Life Sciences). The percentage of specific lysis in each sample was calculated according to the following formula: % Specific release=([experimental release−spontaneous release]÷[maximum release−spontaneous release])×100.

The initial evaluations of the effects of sialic acid focused on in vitro ADCC activity of the two pairs of natural variants. Ab1-29 and Ab1-20 were incubated at varying concentrations with Europium-labeled, Ag1-expressing target cells. As shown in FIG. 6A, there was a clear difference in cytotoxic activity, wherein Ab1-29, with higher levels of Fc sialylation, was required at approximately 7-fold higher concentrations than Ab1-20 in order to trigger cell lysis to the same extent. The results showed that the Ab1 sublot that was enriched for sialylated glycoforms, Ab1 MAAB, was less potent than the unmodified Ab1 PBS. Approximately 3 times as much of the Ab1 MAAB-43% material was required to achieve the same amount of lysis as the Ab1 PBS-29% sample. Experiments with Ag5-expressing target cells showed the same pattern for the pair of Ab2 natural variants. In order to achieve the same degree of cell lysis as the Ab2-0 variant with no detectable sialic acid, an approximately 6-fold higher concentration of Ab2-26 was required (as shown in FIG. 6B). Thus, the effect of natural glycosylation variation on this measure of ADCC is not Ab or target specific.

In a representative experiment to compare the ADCC activity of sublots of the Ab1 that differ in their sialic acid content following a lectin-based fractionation, Ab1 MAAB (43% sialylated) was compared to the unmodified Ab1 lot from which it was derived (Ab1 PBS). In a second experiment to compare Ab1 sublots that differed in sialic acid content, Ab1 WGAT (29% sialylated), Ab1 WGAR (40% sialylated), and Ab1 WGAB (32% sialylated) were compared to each other.

The results of the assay also demonstrate an inverse relationship between sialic acid content and potency in the ADCC assay regardless of the manner in which the Ab was prepared (FIG. 6C). That is, Ab1 WGAT, which contains about the same amount of sialic acid as the unmodified Ab1, showed the same activity as the unmodified Ab1. However, WGA prepared fractions lost potency with increasing sialic acid content (FIG. 6C).

In an experiment, two samples with more profound differences in sialic acid content were compared, enzymatically-modified Ab1 G2 (0% sialylated) and Ab1 G2S2(hi) (~95% sialylated). Fresh PBMCs were isolated by density centrifugation in Ficoll-Paque. $5 \times 10^5$ PBMCs in a volume of 100 ml were pre-incubated for approximately 10 minutes with varying amounts of untreated Ab1, Ab1 G2S2(hi) (fully galactosylated and sialylated), or Ab7, an isotype-matched, negative control Ab. K2 cells expressing surface bound recombinant human TNF were used as the targets by labeling with 200 mCi of $^{51}Cr$. The labeled cells were added to the PBMC/Ab mix, centrifuged at 1000 rpm for 1 minute, and incubated at 37° C. for 4 hours. This incubation time (4 hours) is known to reveal primarily cell lysis induced by NK cells (within the population of PBMC cells), which express FcγRIIIA, rather than by macrophages, which generally express FcγRI (CD64), FcγRIIA (CD32A), and FcγRIIIA (CD16A). The number of radioactivity in the cell supernatants was then determined using Topcount. The results shown (FIG. 6D) are representative of two independent experiments done using PBMCs from different donors and show more than 10-fold change in potency of cell lysis between Ab that is fully sialylated and one that is almost desialylated.

Other pairs of Ab preparation were also compared in the ADCC assay. WGA lectin fractions prepared from galactosylated Ab2 were evaluated in ADCC assays using Ag2-expressing target cells. Again, the higher sialylated material was less active, although there was only a 4-fold difference in their $EC_{50}$ values despite their dramatic difference in sialic acid content (5% vs 67%). By comparison, the WGA lectin fractions made from Ab1 showed the 41% sialylated variant needing to be at approximately 6-fold higher concentrations than the 29% sialylated variant to achieve the same degree of cell lysis.

These results for all three Abs tested consistently showed that higher levels of Fc sialic acid was associated with reduced ADCC activity. Although not quantitative, the differences between the magnitude change in ADCC activity and in sialic acid content of the Ab preparations, there was a consistent relationship within the panel of four Ab1 variants, where the $EC_{50}$ values were typically 0.3 ng/ml, 2 ng/ml, 2 ng/ml and 10 ng/ml for Ab1-20, Ab1-29, Ab1-WGA-29, and Ab1-WGA-41, respectively. The results with the lectin fractions also confirmed that sialylated Ab preparations contain molecular species with varying levels of ADCC activity. It is noteworthy that, with the exception of Ab3-0 and Ab3-26, the variants analyzed here tended not to show differences in the maximum level of lysis achieved.

Since this method of measuring ADCC activity is primarily mediated by FcγRIIIA-positive NK cells, the data imply that, whereas the presence of sialic acid in the Fc oligosaccharide enhances binding to FcγRI, its presence significantly diminishes binding to FcγRIIIA.

Example 4

Binding to High-Affinity Cellular FC Receptor

Binding of test Abs that differed in sialic acid content to high-affinity human Fc receptor, FcγRI (CD64), was measured using a competition binding format on U-937 cells, a human monocytic cell line. U-937 cells were cultured in RPMI 1640 medium with 2 mM L-glutamine, 1 mM sodium pyruvate, and 10% FBS in T flasks and maintained in an incubator with 5% CO2 at 37° C. Ab2, a mouse/human IgG1 chimeric Ab, was iodinated using IODO-Gen precoated iodination tubes to a specific activity of 17.2 mCi/mg. U-937 cells were resuspended at $6 \times 10^6$ cells/ml with fresh culture media, and then seeded into Millipore 96-well tissue culture plates with filters at a density of $3 \times 10^5$ cells per well. The cells were not pre-treated to induce higher FcγR expression. Iodinated Ab2 was pre-mixed with varying amounts of unlabeled Mab competitor (the test samples) using culture medium as diluent, in a volume of 50 µl. The mixtures were then added to a 50 µl culture of U-937 cells to give a final iodinated Ab2 concentration of 0.2 ng/ml. Cells were then incubated at 4° C. for 16 hours. Unbound IgG was removed by washing with medium and aspirating three times using a plate vacuum system. The number of counts bound to the cells was determined using a gamma counter.

Figure 7:
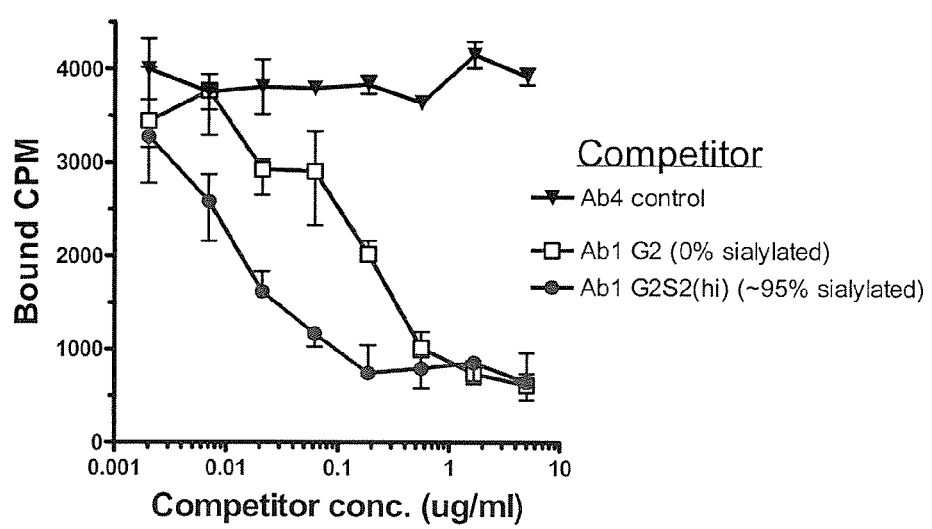
FIGS. 7A and B are graphs showing the competitive binding of various IgG antibody samples to human FcγRI (CD64) receptor on U-937 cells (A) Ab1 G2 (fully galactosylated and unsialylated) and Ab1 G2S2(hi) (fully galactosylated and fully sialylated) differ only by the absence and presence of sialic acid, (B) two different lots of Ab3 differ in the amount of charged oligosaccharide species (sialic acid-containing species), being either 2% or 42% of the total oligosaccharide.
Figure 7:
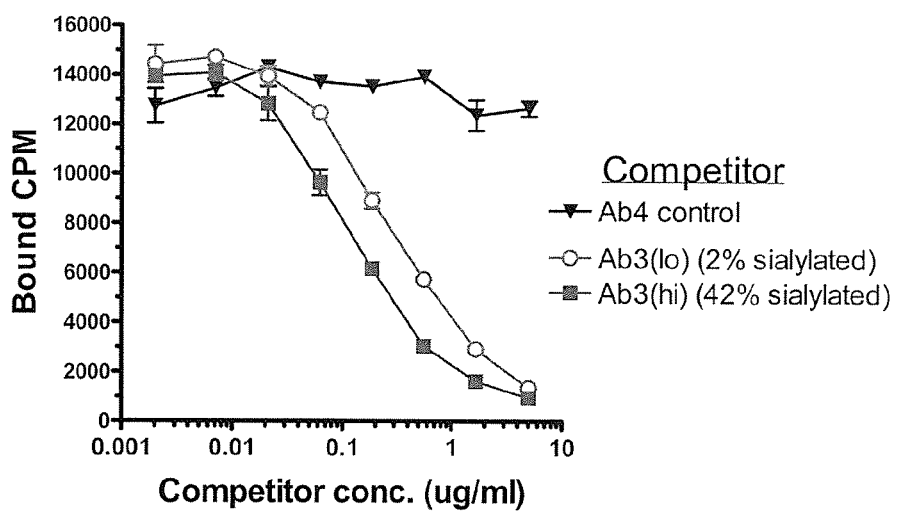

FIG. 7A shows that, compared to Ab1 G2 (no sialic acid), Ab1 G2S2(hi) (~95% sialylated) bound to the high-affinity FcR (CD64) on U-937 cells with 5 to 10-fold higher affinity, i.e., Ab1 G2S2(hi) was required at only one-fifth to one-tenth the concentration to give the same degree of inhibition of iodinated Ab2 binding. Ab1 G2 showed no detectable difference from untreated Ab1 (data not shown), the latter being a heterogeneous mixture of different glycoforms, most of which contain less galactose (ie. G0 and G1 glycoforms) than the Ab1 G2 sample.

FIG. 7B shows that two different lots of Ab3 differing in the amount of charged oligosaccharide species (sialic acid-containing species), being either 2% of the total oligosaccharide or 42%, similarly show that the lot characterized as having higher sialic acid content has higher affinity for FcγRI.

Figure 5:
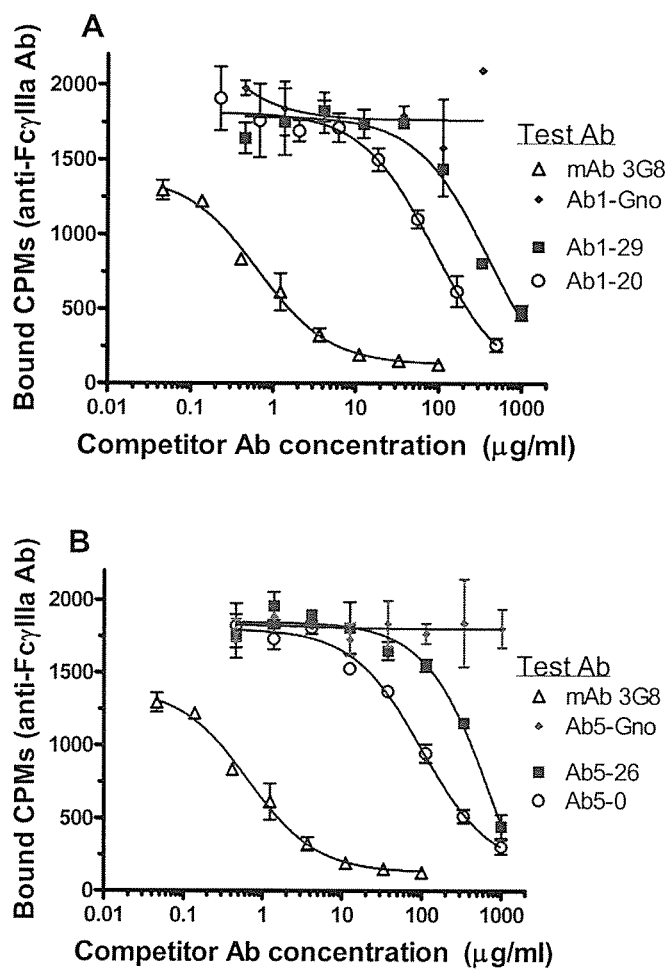
FIGS. 5A-D are graphs of FcγRIIIa binding studies with various test Ab preparations used to compete radiolabeled anti-FcγRIIIa mAb 3G8 at a fixed concentration for binding the NK-cell FcγRIIIa: Ab1 natural glycosylation variants (A); Ab5 natural glycosylation variants (B); Ab1 lectin column fractions (C); and Ab2 lectin column fractions (D).
Figure 5:
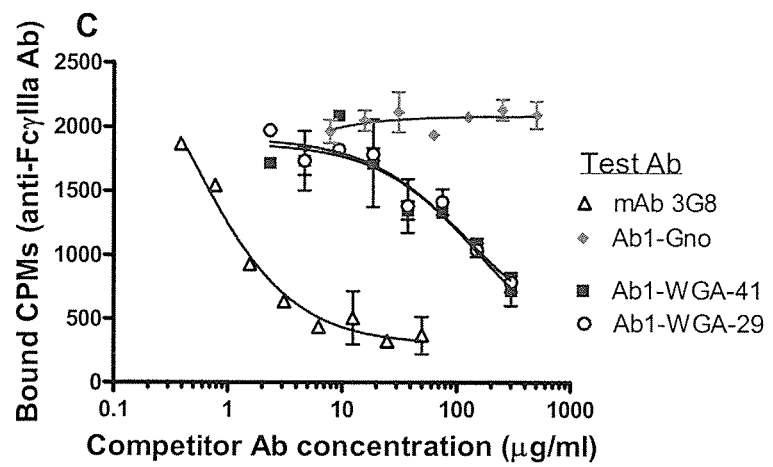
Figure 5:
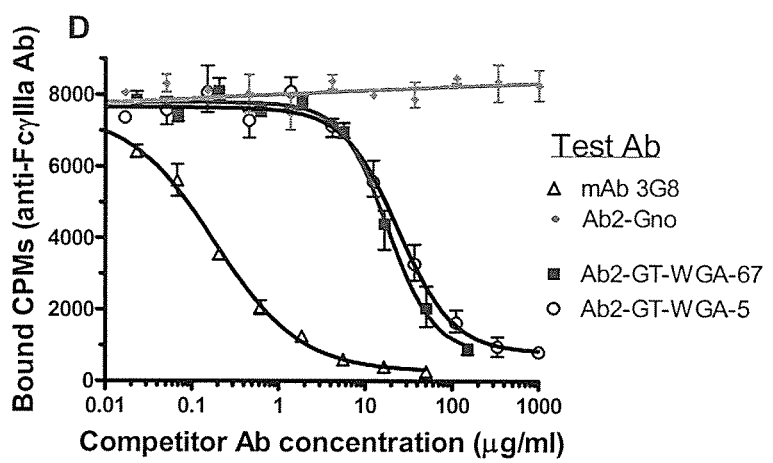

After observing the reduced binding to NK cell FcγRIIIa by antibody preparations with higher sialic acid content for two pairs of natural glycosylation variants of Ab1 and Ab5 (Example 3, FIGS. 5A and B), the possibility that the effect was due to simple electrostatic repulsion between the negatively-charged sialic acid and the negatively-charged cell surface was considered. However, the inverse effect of sialic acid content on binding affinity for the FcγRI receptor on human U-937 cells did not follow the same pattern for Ab5 or other Abs (data not shown).

It should be noted that, whereas the two Ab1 samples differ in the absence/presence of the NANA form of sialic acid, the two Ab3 samples are believed to differ in the amount of the NGNA form of sialic acid (produced in mouse host cells).

Example 5

Measurement of Serum Half-Life

In the present example, an Fe-containing fusion protein comprising an N-terminal peptide fused to an antibody variable region sequence and a human IgG1 hinge, CH2 and CH3 domains expressed in mouse myeloma cells was treated to form the fully sialylated (G2S2) form. Normal female CD1 rats (4 per treatment group) were given an intravenous injection of either the unmodified form of the FcP1, which contained Fc oligosaccharides that were 5% sialylated, or the fully sialylated version (~98% sialylated) were injected separately into groups of female CD1 rats intravenously. Blood was collected by retro-orbital bleeds at 1 hours, 5 hours, 24 hours, 72 hours, 7 days, 14 days, and 21 days, and then a terminal blood collection was taken by cardiac puncture from $CO_2$-anesthetized animals on day 28. Serum was prepared from the blood samples and the concentration of human Fc in the serum measured using a colorimetric ELISA. Briefly, 96-well EIA plates were first coated with polyclonal goat anti-human Fc antibodies. Varying dilutions of the serum samples were incubated in the wells for 1 hour at room temperature. Unbound protein was removed by washing, and bound human Fc detected using enzyme-conjugated goat anti-human IgG antibodies, followed by the appropriate color substrates.

The results of the study are shown in FIG. 8. The calculated area under the curve (AUC) was $95\pm1.6$ day·ng/ml×$10^{-3}$ for the unmodified antibody and $48\pm1.9$ day·ng/ml×$10^{-3}$. This showed that a higher degree of sialylation in the Fc oligosaccharide was associated with a faster rate of clearance in normal rats.

Figure 9:
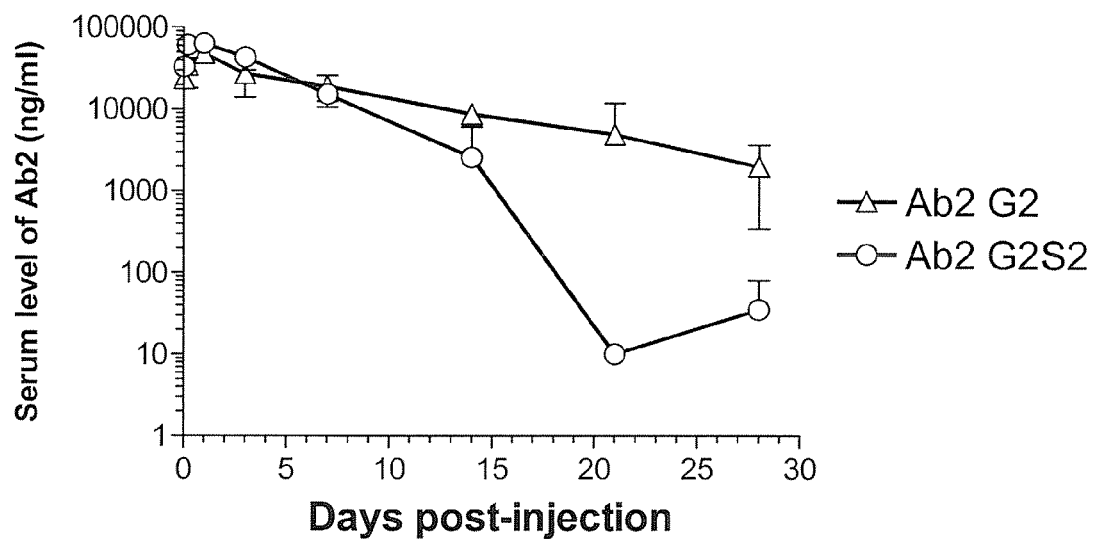
FIG. 9 is a graph showing the relationship between time after administration and serum concentration of the Fc-portion of a fully sialylated, Ab2 G2S2, or fully asialylated, Ab2 G2, by enzymatic methods as described.

In a second experiment, normal mice were injected with a single 3 mg/kg dose of Ab2 enzymatically modified to be either fully asialylated (G2) or fully sialylated (G2S2). Human Fc in the serum was monitored and measured using colorimetric ELISA as described above. The results of this experiment are shown in FIG. 9. After a period of approximately one week, the Ab2 G2S2 began to be cleared more rapidly from the serum of the mice and by 20 days the Ab2 G2S2 remaining in the serum was approximately 1000-fold less than the concentration of Ab2-G2.

Clearance of Ab1 Sialic Acid Variants from Systemic Circulation in Mice.

Another direct measurement of the effect of sialic acid content was made by quantitating the rate of clearance of individual glycosylation species from serum after injection of a sample containing a heterogeneous mixture of glycan species attached to an Ab1.

The same heterogeneously glycosylated preparation of Ab1 was injected i.p. into 18 normal, 8-10 week old Balb/c mice at a dose of 20 mg/kg. Blood was collected from 6 mice on day 3, another 6 mice on day 14, and the final 6 mice on day 28. Serum was prepared from each blood sample and Ab1 re-purified from the serum using an anti-Id affinity column specific for Ab1 V regions. The structures of the Fc glycans of the re-purified Ab1 samples were then analyzed by HPLC analyses and the relative proportion of various glycoforms determined as described previously herein.

It was found that the galactosylated glycoform that lacks sialic acid (G2S0) maintains its relative abundance over the 4-week period in the mice, whereas the Ab glycoforms containing glycans with 1 sialic acid (G2S1) and the glycoforms with 2 sialic acids (G2S2) cleared at a faster rate. Thus, fully sialylated Fc-containing proteins have a shorter serum half-life than asialylated or partially sialylated compositions.

Example 6

Sialic Acid Content and Antibody Avidity

The results described herein support the theory that a change in sialic acid content of the Fc-glycan of the Fc-domain (dimerized hinge-CH2-CH3) will impact the entire protein. With respect to the bivalency of antibodies and fusion proteins comprising a glycosylated Fc, the effects may be manifested in the avidity of the protein for a specific target. The experiments in this example were performed to test this theory and, further, demonstrate the specific effect of sialic acid content on target binding affinity.

Binding to Cell-Surface Antigen.

The same Ag-expressing cell lines used in the above-described ADCC assays were used in binding assays to test for differences among sialic acid variants in their antigen binding avidity. Assays were performed in a competition format, in which one of the radiolabeled Abs (either Ab1, Ab2, or Ab5), kept at a fixed concentration, was incubated with the Ag-expressing cells in the presence of varying amounts of unlabeled test Abs. Iodinated Abs, prepared by the Iodogen method, were generally at a specific activity of 10 uCi/ug.

The surface TNF-expressing cells were seeded in 96-well tissue culture plates at 50,000 cells per well, and Ag2-expressing cells at 180,000 cells per well, in IMDM medium with 5% FBS. The appropriate $^{125}$I-labeled Ab was premixed with titrating amounts of test Abs and the mixture added to the appropriate Ag-expressing cells. The plates were incubated at RT for 2 hours to allow Ab binding to the cells. The cells were then washed three times with IMDM, 5% FBS to remove unbound Ab, and the number of counts bound to the cells determined using a gamma counter.

For Ab5 variants, Ag5-expressing cells were seeded in 96-well tissue culture plates at 186,000 cells per well in 50 μl of DMEM, 10% FBS. $^{125}$I-labeled Ab2 was premixed with titrating amounts of test Ab and 50 μl of the mixture added to the Ag-expressing cells. The plates were incubated at 4° C. for 16 hours to allow Ab binding to the antigen on the cells. The cells were then washed three times with DMEM, 10% FBS to remove unbound Ab, and the number of counts bound to the cells determined using a gamma counter. Samples were tested in duplicates or quadruplicates, and results shown are representative of 3 or 4 independent experiments. The difference in binding between these test samples was significant (P<0.0001 for graphs a, c, and d) as determined by extra sum of squares F-test.

Figure 10:
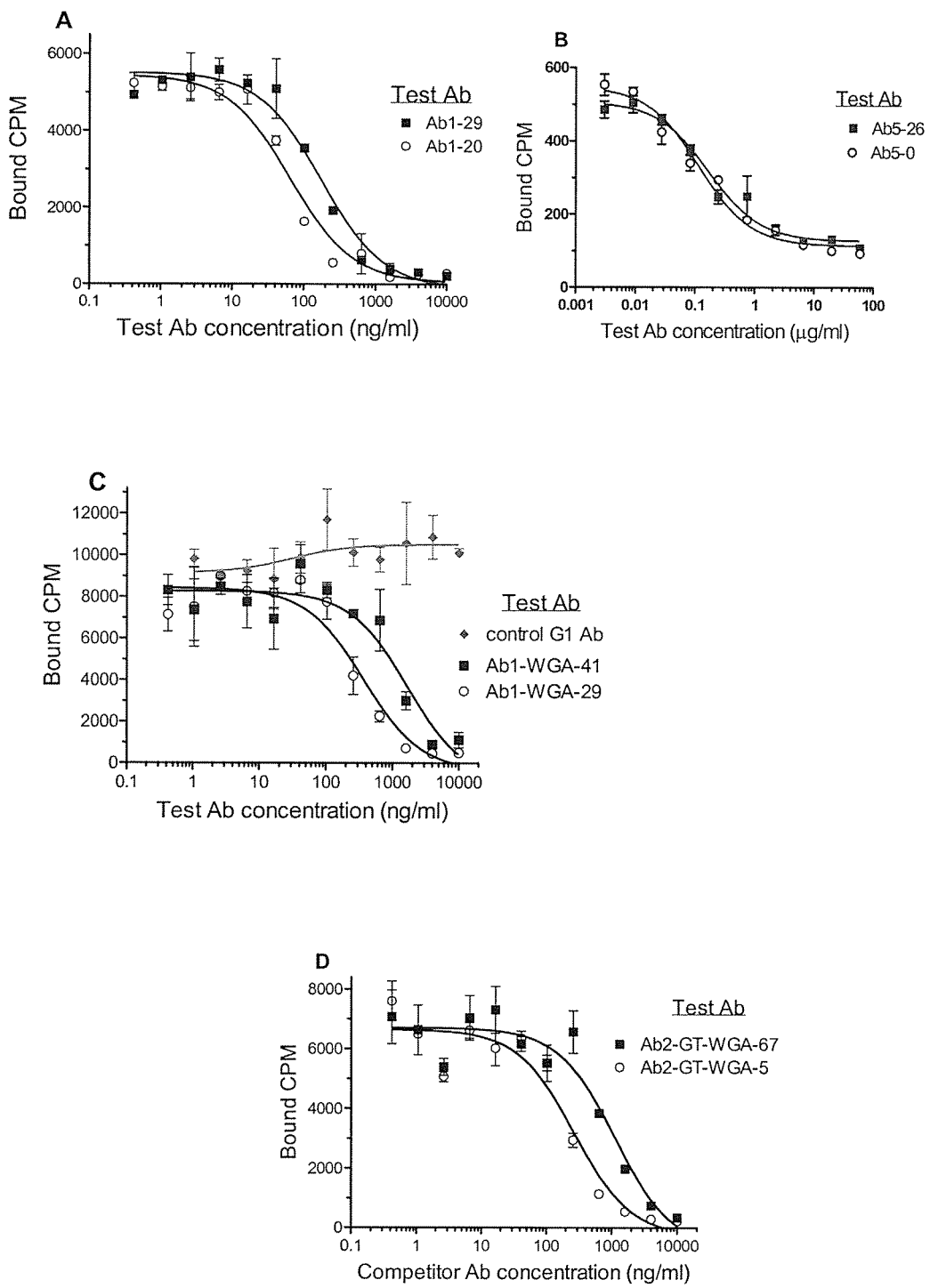
FIG. 10A-D are graphs showing the effect of sialic acid in Ab preparations on affinity for target ligand on the cell surface by competitive binding with radiolabeled Ab: (A) Ab1 natural variants, (b) Ab5 natural variants, (C) Ab1 lectin-column fraction variants, and (D) Ab2 lectin-column fraction variants. Samples were tested in duplicates or quadruplicates, and results shown are representative of 3 or 4 independent experiments. The difference in binding between these test samples was significant ($P<0.0001$ for graphs A, C, and D) as determined by extra sum of squares F-test.

The results are shown in FIG. 10A-D: binding by radiolabeled Ab1 to Ag1-expressing cells in the presence of unlabeled Ab1 natural variants as competitors (FIG. 10A); binding by radiolabeled Ab5 to Ag5-expressing cells in the presence of unlabeled Ab5 natural variants as competitors (FIG. 10B); binding by radiolabeled Ab1 to Ag1-expressing cells in the presence of unlabeled Ab 1 lectin-derived variants as competitors (FIG. 10C); binding by radiolabeled Ab3 to Ag3-expressing cells in the presence of unlabeled Ab3 lectin-derived variants as competitors (FIG. 10D).

Ab Binding to Solid Phase Ligand.

Recombinant soluble TNF or anti-Id2 was coated on EIA plates by adding 50 µl of Ag or anti-Id Ab at 1 µg/ml in PBS to each well and incubating the plates at 4° C. overnight. The wells were washed and then pre-treated with 50 µl of 1% BSA, 0.125% gelatin in PBS for 1 hour at RT to minimize non-specific binding. $^{125}$I-labeled Ab1 or $^{125}$I-labeled Ab3 was premixed with titrating amounts of respective test Ab preparations in IMDM, 5% FBS, and 50 µl of the mixture added to the target-coated wells. The final concentration of radiolabeled Ab was 100 ng/ml in all wells. The plates were incubated at RT for 2 hours to allow Ab binding to the coated targets. Wells were washed to remove unbound Ab and the number of counts bound determined using a gamma counter.

Binding of Plate-Coated Abs to Soluble Antigen.

96-well plates were coated with sialic acid variants of Ab1 or Ab3 and then incubated with varying amounts of radiolabeled soluble antigen as follows: (a) binding of radiolabeled soluble Ag1 to plate-coated Ab1 natural variants, (b) binding of radiolabeled soluble Ag1 to plate-coated Ab1 lectin-fractionated variants, and (c) binding of radiolabeled soluble Ag3 to plate-coated Ab3 lectin-fractionated variants. Parallel incubations with radiolabeled Ag and 100-fold excess unlabeled Ag were done to determine nonspecific binding. Samples were tested in triplicates. Ab2 variants were not analyzed due to unavailability of soluble Ag2.

Statistical Analyses.

A difference in potency between antibody variants was analyzed by comparison of the curves using simultaneous 4-parameter logistic regressions with a common minimum, maximum and slope following a preliminary test for slope and range given a common plateau for a zero concentration (i.e., always assuming without testing a common "bottom" for increasing curves and common top for decreasing curves). Significance testing was done with the extra sum of squares F-test in GraphPad Prism v4. A P value of <0.05 was considered to be significant. Analyses on CPM were weighted inversely by $CPM^2$ because the standard deviation of CPM increases proportionally to its mean (i.e., the CPM coefficient of variation, CV is unrelated to the mean).

Results

Antigen binding experiments performed in a competition format with the same Ag-expressing targets cells that were used in the ADCC assays unexpectedly showed Ab1-29 to consistently bind cell-surface antigen with about 3-fold less affinity than Ab1-20 (FIG. 10A). Ab5-26, in contrast, showed an affinity that was indistinguishable from Ab5-0 (FIG. 10B). The same analyses performed with the two pairs of lectin-derived variants showed similar results to the Ab1 natural variants, i.e., the higher sialylated Ab1-WGA-41 was required at 4 to 6-fold higher concentrations than the lesser sialylated Ab1-WGA-29 to achieve the same degree of competitive binding (FIG. 10C), and the higher sialylated Ab2-GT-WGA-67 was required at 4 to 6-fold higher concentrations than the lesser sialylated Ab2-GT-WGA-5 (FIG. 10D).

Figure 11:
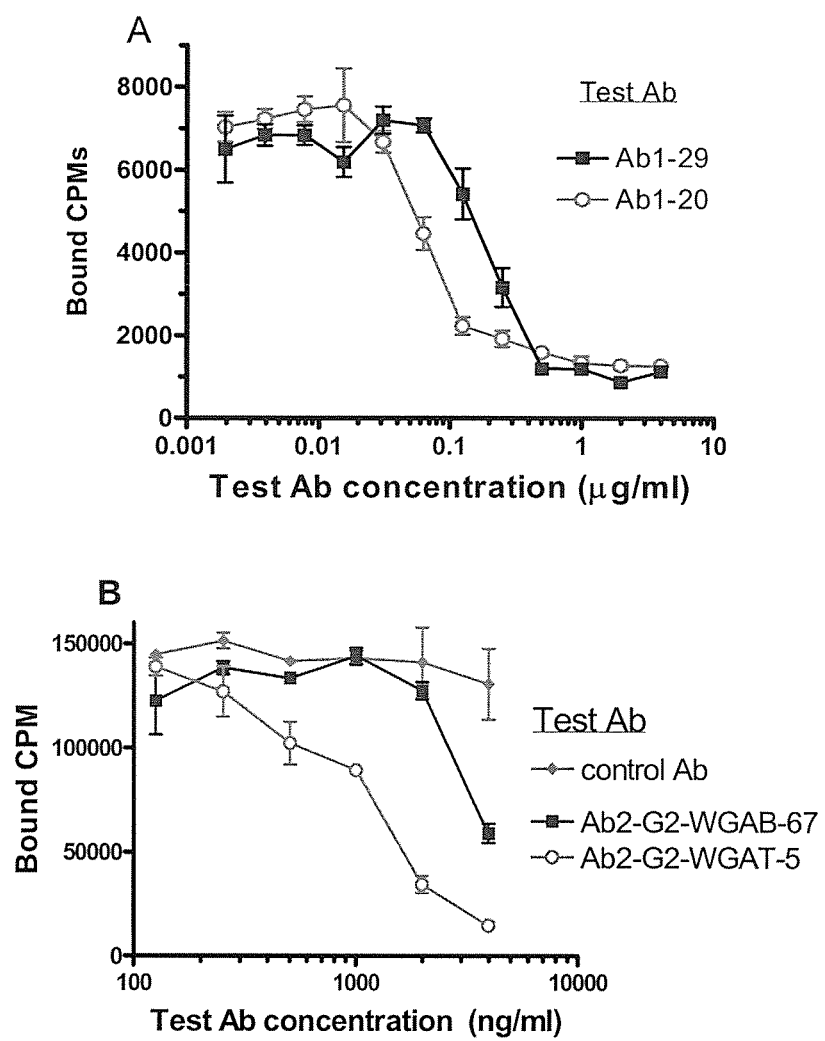
FIG. 11A-B are graphs showing the effect of sialic acid in Ab preparations on affinity for target ligand coated on EIA plates: (A) Ab1 natural variants binding to TNF, (B) Ab2 binding to an anti-Id antibody.

Interestingly, the same pattern of decreased binding by Ab1 and Ab2 variants with higher amounts of sialylation was also observed in experiments analyzing binding to targets (soluble recombinant antigen or anti-Id Ab) that were immobilized on 96-well EIA plates (FIGS. 11A and B). These results showed that differences in the extent of Fc sialylation may impact binding to antigen as well as to FcγRIIIA, but that the extent of sialylation does not impact antigen binding of all Abs.

From the data on immobilized target binding, it is believed that increased Fc sialylation may serve to reduce Ab hinge region flexibility. In the case of Ab1 and Ab2 binding to cell-surface antigen, reduced hinge flexibility could lead to more monovalent binding and less bivalent (high avidity) binding to antigen depending on the spacing of antigen epitopes on the solid support or cell surface. The hinge region of Ab5 may also have reduced flexibility, but flexibility may not be needed for this Ab to achieve maximal binding to Ag5.

Figure 12:
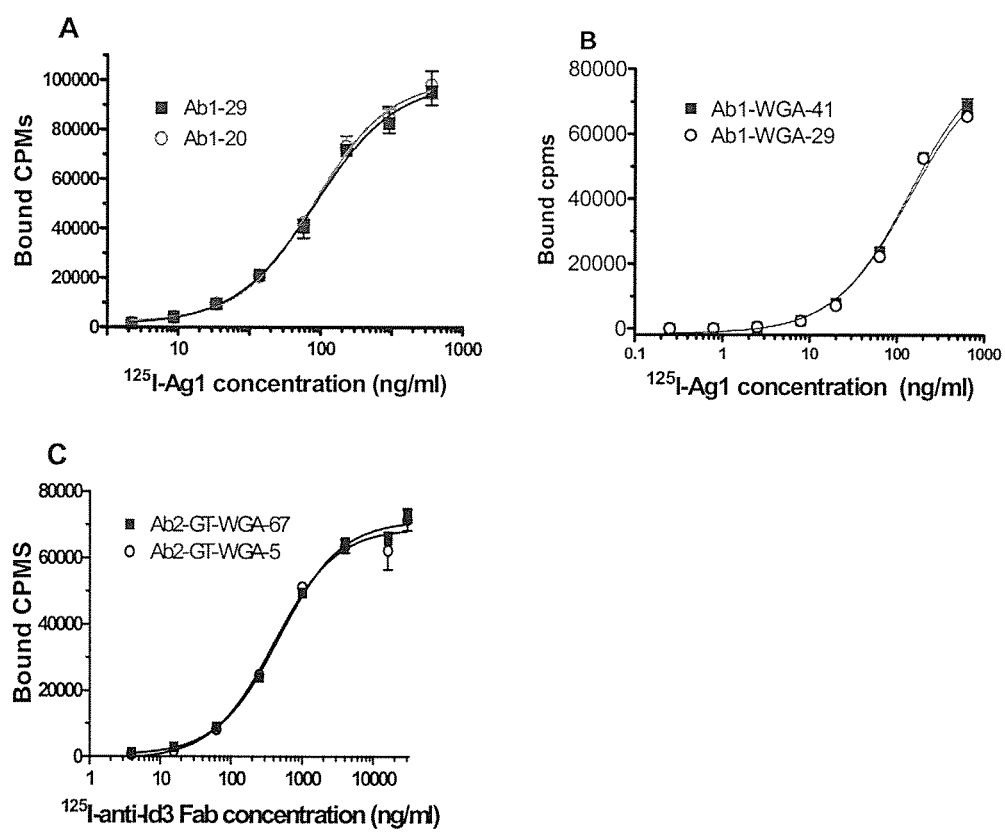
FIG. 12A-C are graphs showing the effect of sialic acid in Ab preparations on affinity for target ligand presented as radiolabeled soluble antigen to surface bound Ab: (A) Ab1 natural variants, (B) Ab1 1 lectin-column fraction variants, and (C) Ab2 lectin-column fraction variants. Parallel incubations with radiolabeled Ag and 100-fold excess unlabeled Ag were done to determine nonspecific binding. Samples were tested in triplicates.

In order to differentiate between whether the Ab flexibility effects or intrinsic binding affinity changes were affected by Fc sialylation, the binding of Ab to soluble ligand was tested as a measure of purely monovalent binding affinity. The results indeed showed that for the three pairs of sialic acid variants that showed differences in binding to cell-surface antigen, there were no detectable differences observed between pairs of variants in their binding to soluble targets (FIG. 12A-C). Taken together, these results demonstrated that differences in binding to immobilized targets (cell-surface or plate-coated) were not due to differences in intrinsic affinity between each Fab atm and the target. Therefore, the differences between the Ab1 and Ab2 sialic acid variants in their binding to immobilized targets is due to differences in the extent of bivalent binding to the cells.

Example 7

Preparation of a Vector for Secretion of Sialidase

Sialidase Expression Plasmid Assembly.

A nucleic acid sequence encoding the catalytic domain of the *Arthrobacter ureafaciens* sialidase, residues 40 to 535 of GenBank accession number AY934539, was synthesized based on that sequence. The synthesized gene (SEQ ID NO: 2) encoding the human growth hormone signal sequence-*Arthrobacter ureafaciens* catalytic domain fusion (SEQ ID NO:1 with the signal sequence as the first 26 amino acids and the catalytic domain the remaining 494 amino acids) was cloned in plasmid p2815 using unique BamH I and Not I restriction sites. This plasmid possesses a CMV promoter, coding sequence for human growth hormone signal sequence to affect secretion, and a neomycin resistance gene for stable selection. The coding sequence for the enzyme catalytic domain ligated to the hGH signal coding sequence (SEQ ID NO: 1) was verified by restriction enzyme digestion and sequencing.

Transient and Stable Transfection.

For transient transfection, HEK293 cells were transfected with 15 ug of purified plasmid p3629 or control plasmid (empty vector) using Lipofectamine 2000. Plasmid DNA and 90 uL of Lipofectamine 2000 was diluted in Optimem, combined, and then incubated for 20 minutes at room temperature. The transfection cocktail was then added to 70% confluent HEK293 cells in growth media overnight. The next day, growth media was replaced with 293SFM media, and the cells incubated for 5 days for media harvest and analysis. For stable transfection, C168M cells were electroporated with 10 ug of p3629 that had been linearized by restriction digestion with Bgl II. Transfected cells were maintained in growth media with 700 ug/mL of Geneticin antibiotic to select for stable transfectants. Antibiotic resistant clones were expanded, and assayed for sialidase.

Sialidase Activity Assay.

Sialidase activity was assayed using 2'-(4-methylumbelliferyl)-a-D-N-acetylneuraminic acid. A fluorometic assay on cell supernatant from viable cell cultures was performed by mixing it with 200 uL of 150 uM 2'-(4-methylumbelliferyl)-α-D-N-acetylneuraminic acid in 100 mM citrate-phosphate buffer, ph 6.5 at 37° C., followed by the addition of 2 mL of 0.5M $Na_2CO_3$ to stop the reaction. Excitation was performed at 366 nm and emission at 446 nm. Fluorometric units were normalized against viable cell counts. Alternatively, sialidase activity in culture medium was determined by overnight incubation of sialylated Remicade with media from transfected cells, and assaying for sialic acid as described below.

Sialic Acid Determination.

Sialidase activity was determined by assaying for sialic acid removal from purified antibody after incubating with the cell culture supernatants. The N-linked oligosaccharides were released by treating IgG samples (0.05-05 mg in 0.1 ml) with PNGase F in 20 mM Tris-HCl buffer, pH 7.0 at 37° C. for 4-6 hrs. An aliquot of this solution (~0.01 ml) was passed through a column containing cation exchange resin and analyzed by MALDI-TOF-MS as described previously ( ). The remaining portion of the sample was subjected to reductive amination with anthranilic acid and subsequent analysis by HPLC as described by Anumula. Briefly, a solution of 4% sodium acetate $3H_2O$ (w/v) and 2% boric acid (w/v) in methanol was prepared first. The derivatization reagent was prepared fresh by dissolving ~30 mg of anthranilic acid (Aldrich) and ~20 mg of sodium cyanoborohydride (Aldrich) in 1.0 ml of methanol-sodium acetate-borate solution. IgG derived oligosaccharides (<3 nmol in 20-50 µl of water) were mixed with 0.1 ml of the anthranilic acid (AA) reagent solution in 1.6 ml polypropylene screw cap freeze vials with 'O" rings (Sigma) and capped tightly. The vials were heated at 80° C. in a heating block (Reacti-Therm, Pierce) for ~1 hour. After cooling the vials to room temperature, the samples were diluted with water to bring the volume to ~0.5 ml. Derivatized oligosaccharides were purified as described previously.

Antibody Purification.

Recombinant antibodies expressed from stable transfected cells were purified by Protein A affinity chromatography. Cell supernatants were diluted with 10× Protein A buffer (0.2M Tris, 1.4M NaCl, 10 mM EDTA, pH8.5) to 1×, and purified on a 1 mL protein A column. The eluted antibodies were dialyzed into PBS, pH 7.2, before further analysis.

Antibody Dependent Cellular Cytotoxicity Assay (ADCC).

Target cells for assays involving Ab1 and Ab3 were prepared at Centocor by transfecting Sp2/0 mouse myeloma cells with transmembrane form of Ag1 and Ag3, respectively. Both Ag1-expressing and Ag3-expressing cell were cultured in IMDM containing heat-inactivated FBS, 2 mM L-glutamine, 1 mM sodium pyruvate, 0.1 mM non-essential amino acids. Adherent cells expressing Ag2 were obtained from ATCC and cultured in DMEM medium containing 10% FBS, 2 mM L-glutamine, 1 mM sodium pyruvate and 0.1 mM non-essential amino acids. All cells were passaged twice a week and maintained in log phase growth. Culture media and supplements were purchased from Gibco (Invitrogen).

On the day of the assay, Ag-expressing myeloma target cells were centrifuged and washed once with PBS. Adherent Ag2-expressing target cells were removed with trypsin and washed twice. Cells were adjusted to $1\times10^6$ cells/ml with culture medium and 15 µl of BATDA ((Bisacetoxymethyl)-2,2':6'2"-terpyridine-6,6"-dicarboxylate) fluorescent labeling reagent (in Delfia EuTDA Cytotoxicity Kit, Perkin-Elmer Life Sciences; Blomber, K. et.al) was added to 5 ml of cells. Cells were incubated for 30 minutes at 37° C. with occasional shaking; then washed twice with media. Immediately prior to mixing with effector cells, targets cells were centrifuged and resuspended at $2\times10^5$ cells/ml in culture media.

Peripheral blood mononuclear cells (PBMC) effector cells were isolated from heparinized blood of healthy donors. Blood samples were diluted with phosphate buffered saline (PBS) and PBMC were isolated by density gradient centrifugation on Ficoll-Hypaque (Amersham). After centrifugation, PBMC were collected, washed twice, and kept overnight in culture media at 37° C. with 5% $CO_2$. On the following day, PBMC were collected, washed and resuspended in media at $1\times10^7$ cells/ml.

For the cytotoxicity assays, antibody dilutions in 100 µl culture media were added to a round bottom 96 well plate. Fifty µl of effector cells and 50 µl of BADTA-labeled target cells were added to the Ab dilutions at an effector to target cell ratio of 50:1. The plate was centrifuged briefly to bring effectors and targets in contact with each other, and then incubated for 2 h at 37° C. in a 5% $CO_2$ atmosphere. After incubation, 20 µl of supernatant were transferred to wells of a flat bottom 96 well plate and 200 µl aliquot of Europium enhancement solution (in Delfia Cytotoxicity kit) was added to each well. After shaking the plate for 10 min, fluorescence was measured in a time-resolved fluorometer (EnVision instrument, Perkin-Elmer). The percentage of specific cytotoxicity was calculated as (experimental release-spontaneous release)/maximum release–spontaneous release)×100. Spontaneous release was determined by incubating the targets with media instead of effector cells, and maximum release was determined by incubating the targets with 10 ul of lysis solution containing digitonin (in Delfia EuTDA Cytotoxicity kit).

Results and Discussion

Figure 13:
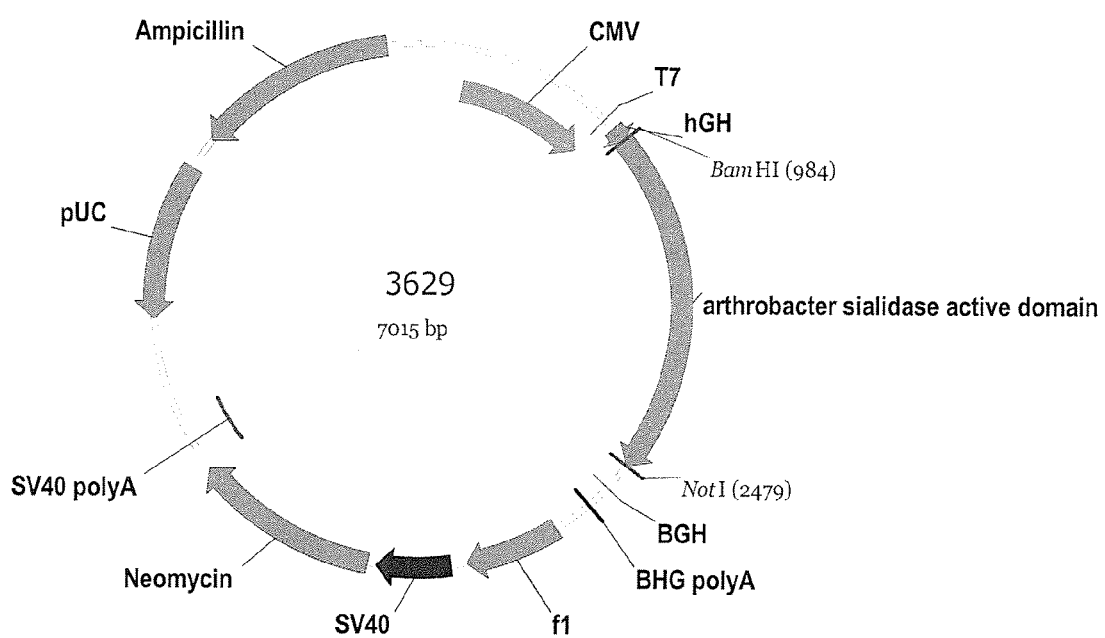
FIG. 13 is a schematic representation of expression plasmid p3629 constructed to express the catalytic domain of the *Arthrobacter ureafaciens* sialidase A linked to the hGH (human growth hormone) signal sequence with restriction enzyme sites used for cloning into the parent vector, p2815, indicated.

Expression vector p3629 (FIG. 13) was constructed, and allows for the expression of the *Arthrobacter ureafaciens* sialidase A catalytic domain in mammalian cells. The coding sequence for the human growth hormone leader sequence was operatively linked to the catalytic domain of the enzyme in order to force extracellular secretion of the sialidase A. HEK293 cells were transiently transfected with the expression plasmid, and supernatant collected for sialidase activity on purified anti-TNFα antibody. Antibody was incubated overnight with conditioned media from p3629 transfected cells, or control plasmid transfected cells. HPLC analysis of oligosaccharides released from the antibody after incubation with the conditioned supernatant was undetectable in all except the glycans released from the control transfected parental cell line. Therefore, sialidase activity was present only in the p3629 transfected cell supernatant, and not the control transfected supernatant.

Example 8

Co-Expression of Antibody and Sialidase

The goal of these studies was to generate a host cell line capable of secreting a sialidase enzyme into the culture media, which could be further transfected with antibody encoding sequence thereby producing glycosylated antibody which would be desialylated. The mouse myeloma cell line, C168M, that expresses an antibody was transfected with vector prepared in Example 7, p3629, and stable clones selected and screened for sialidase activity in supernatant. As shown in Table 2 below, of the 17 clones assayed fluorometrically (MFU) in this experiment, six were positive for sialidase activity and sialidase expression persisted over 6 weeks, indicating stable clones.

TABLE 2

| Clone No. | Sialidase Activity-primary clones (MFU) | Sialidase Activity 6 weeks (MFU) |
|---|---|---|
| WT |  | 0 |
| 1 | 0 |  |
| 2 | 0 |  |
| 3 | 332 | 7536 |
| 4 | 0 |  |
| 5 | 924 | 11544 |
| 6 | 0 |  |
| 7 | 0 |  |
| 8 | 0 |  |
| 9 | 0 |  |
| 10 | −0 |  |
| 11 | 0 |  |
| 12 | 6307 | 23140 |
| 13 | 57 | 519 |
| 14 | 26 |  |
| 15 | 305 | 6408 |
| 16 | 0 |  |
| 17 | 942 | 1765 |

Further analysis of purified antibodies from the sialidase A positive clones by SDS-PAGE indicated that they were still expressing intact antibody, and expression of the sialidase did not affect expression levels. Carbohydrate analysis of the antibodies indicated that all clones contained less then 2% sialic acid, compared to antibody from a non-sialidase transfected host cell, which possessed almost 15% sialic acid (Table 3).

TABLE 3

|  | Sialic acid content (%) | Fucose content (%) | ADCC EC40 (ng/mL) | ADCC max lysis (%) |
|---|---|---|---|---|
| Control transfected | 14.8 | 90 | 39.1 | 37.3 |
| Clone 3 | 1.6 | 94 | 5.7 | 64.3 |
| Clone 5 | 0.76 | 85 | 24.9 | 47.0 |
| Clone 12 | 1.3 | 92 | 45.2 | 41.9 |
| Clone 13 | 2.77 | 65 | 22.3 | 49.0 |
| Clone 15 | 1.36 | 80 | 55.2 | 41.8 |
| Clone 17 | 1.6 | 73 | 8.9 | 43.9 |

Figure 14:
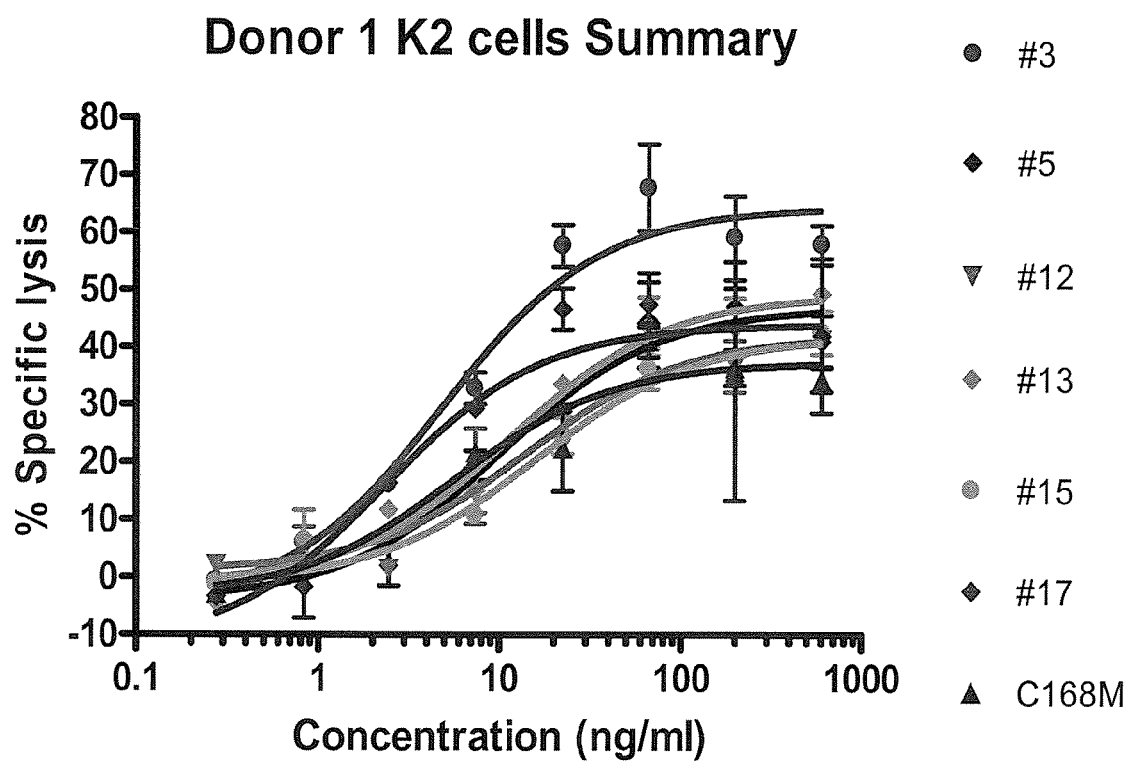
FIG. 14 is a plot representing antibody dependent cellular cytotoxicity (ADCC) activity of purified antibody from cell lines expressing secreted sialidase catalytic domain; Clones 3, 5, 12, 13, and 17.

The low sialic acid antibodies from clones over-expressing the sialidase were assayed for enhanced ADCC activity compared to WT C168M (FIG. 14). As seen in Table 3, some of the samples showed lower EC40s and higher maximum lysis then wild type anti-TNFα antibody, indicating that the lower sialic acid content has an effect on the biological properties of this antibody.

An expression plasmid has been designed that will secrete the catalytic domain of the *Arthrobacter ureafaciens* sialidase A enzyme into the mammalian cell culture media. This secreted enzyme is active in cell supernatants, and is capable of removing sialic acid residue from N-linked oligosaccharides present in the Fc region of antibodies. Stable transfection of cell lines expressing antibodies with this expression construct results in clones that secrete sialidase A activity into culture supernatant, along with antibody. The antibodies recovered from these cell cultures contain less sialic acid which translates into functional improvements in ADCC activity. These results suggest that the method can be used to generate host cells that express recombinant glycoproteins and used to create cultures for minimally sialylated glycoconjugates.

Example 9

CHO Expression of Sialidase

CHO cells are important host cells for the manufacture of biopharmaceuticals. The p3629 (FIG. 13) plasmid was used to stably transfect a CHO cell line capable of being further transfected with a vector for expression of a therapeutic protein, such as an antibody.

CHO cells (C1835A) were transfected with 30 ug of p3629 that had been linearized by restriction digestion with Bgl II using FuGene 6 (Roche, Inc.). The transfected cells were maintained in growth media with 700 ug/mL of Geneticin antibiotic (Invitrogen, Inc.) to select for stable transfectants. Antibiotic resistant clones were pooled, expanded, and assayed for sialidase activity.

Sialidase activity was assayed on cell supernatants from viable cell cultures using a fluorophore. To 200 uL of cell supernatant was added 150 uM 2'-(4-methylumbelliferyl)-alpha-D-N-acetylneuraminic acid in 100 mM citrate-phosphate buffer, pH6.5 at 37° C., followed by the addition of 2 mL of 0.5M $Na_2CO_3$ to stop the reaction. Excitation was 366 nm and emission 446 nm. Fluorometric units (FU) were normalized by dividing individual fluorometric reading for each cell line by the total number of viable cells. Sialidase activity in the culture medium, as measured in FU, is shown in Table 4.

TABLE 4

|  | Week 3 | | Week 8 | |
|---|---|---|---|---|
| Dilution | Control | Transfected | Control | Transfected |
| 1 | 1880 | 4004 | 2547 | 7924 |
| 0.5 | 1742 | 2983 | 2276 | 4733 |
| 0.25 | 1566 | 2320 | 1967 | 2915 |
| 0.125 | 1558 | 2046 | 1960 | 2569 |
| 0.0625 | 1489 | 1990 | 1862 | 2139 |
| 0.03125 | 1513 | 1987 | 2036 | 2444 |

As the sialidase activity at 3 weeks and 8 weeks post-selection remained constant or increased over time, the stable expression and secretion of the sialidase enzyme into the culture supernatant was confirmed.

It will be clear that the invention can be practiced otherwise than as particularly described in the foregoing description and examples. Numerous modifications and variations of the present invention are possible in light of the above teachings and, therefore, are within the scope of the appended claims.

What is to be claimed:

1. A method for providing a sialidase enzymatic activity in a culture comprising a mammalian cell engineered to express an antibody, comprising transfecting the mammalian engineered cell with a vector encoding a catalytic domain of *Arthrobacter ureafaciens* sialidase enzyme A, wherein the polypeptide is secreted into the culture along with the antibody, whereby the antibody glycans can be acted upon by the polypeptide sialidase enzymatic activity, and wherein one or more of the avidity for multiply localized target proteins, the macrophage or monocyte activation, and serum half-life of the antibody are altered.

2. The method of claim 1, wherein the mammalian cell line is selected from the group consisting of COS-1, COS-7, HEK293, BHK21, CHO, BSC-1, Hep G2, 653, SP2/0, 293, HeLa, YB2/0 or Y3, myeloma, or lymphoma cells, or any derivative, immortalized or transformed cell thereof.

3. The method of claim 2, wherein the antibody is an anti-TNFα antibody and the cell line is C168M.

* * * * *

UNITED STATES PATENT AND TRADEMARK OFFICE
CERTIFICATE OF CORRECTION

PATENT NO. : 8,540,992 B2  Page 1 of 1
APPLICATION NO. : 12/521417
DATED : September 24, 2013
INVENTOR(S) : Naso et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 774 days.

Signed and Sealed this

Fifteenth Day of September, 2015

Michelle K. Lee
*Director of the United States Patent and Trademark Office*

SEQUENCE LISTING

<160> NUMBER OF SEQ ID NOS: 2

<210> SEQ ID NO 1
<211> LENGTH: 520
<212> TYPE: PRT
<213> ORGANISM: Arthrobacter ureafaciens

<400> SEQUENCE: 1

```
Met Ala Thr Gly Ser Arg Thr Ser Leu Leu Ala Phe Gly Leu Leu
  1               5                  10                  15

Cys Leu Pro Trp Leu Gln Glu Gly Ser Ala Pro Thr Pro Asn Ser
             20                  25                  30

Pro Thr Leu Pro Pro Gly Ser Phe Ser Glu Thr Asn Leu Ala Ala Asp
             35                  40                      45

Arg Thr Ala Ala Asn Phe Phe Tyr Arg Ile Pro Ala Leu Thr Tyr Leu
     50                  55                      60

Gly Asn Asp Val Val Leu Ala Ala Trp Asp Arg Pro Gly Ser Ala
 65                  70                  75                  80

Ala Asp Ala Pro Asn Pro Asn Ser Ile Val Gln Arg Arg Ser Thr Asp
                 85                  90                  95

Gly Gly Lys Thr Trp Gly Pro Val Gln Val Ile Ala Ala Gly His Val
                100                 105                 110

Ala Asp Ala Ser Gly Pro Arg Tyr Gly Tyr Ser Asp Pro Ser Tyr Ile
            115                 120                 125

Tyr Asp Ala Glu Ala Asn Lys Val Phe Ala Phe Val Tyr Ser Lys
        130                 135                 140

Asp Gln Gly Phe Gly Gly Ser Gln Phe Gly Asn Asp Asp Ala Asp Arg
145                 150                 155                 160

Asn Val Ile Ser Ser Ala Val Ile Glu Ser Ser Asp Ala Gly Val Thr
                165                 170                 175

Trp Ser Gln Pro Arg Leu Ile Thr Ser Val Thr Lys Pro Gly Thr Ser
            180                 185                 190

Lys Thr Asn Pro Ala Ala Gly Asp Val Arg Ser Asn Phe Ala Ser Ser
        195                 200                 205

Gly Glu Gly Ile Gln Leu Lys Tyr Gly Pro His Lys Gly Arg Leu Ile
    210                 215                 220

Gln Gln Tyr Ala Gly Asp Val Arg Gln Ala Asp Gly Ser Asn Lys Ile
225                 230                 235                 240

Gln Ala Tyr Ser Val Tyr Ser Asp Asp His Gly Val Thr Trp His Lys
                245                 250                 255

Gly Ala Asn Val Gly Asp Arg Met Asp Glu Asn Lys Thr Val Glu Leu
            260                 265                 270

Ser Asp Gly Arg Val Leu Leu Asn Ser Arg Asp Asn Ala Asn Arg Gly
        275                 280                 285

Tyr Arg Lys Val Ala Val Ser Thr Asp Gly Gly Ala Thr Tyr Gly Pro
    290                 295                 300

Val Ser Gln Asp Thr Glu Leu Pro Asp Pro Ala Asn Asn Gly Ala Ile
305                 310                 315                 320

Ala Arg Met Phe Pro Asn Ala Ala Gln Gly Ser Ala Asp Ala Lys Lys
                325                 330                 335

Leu Ile Phe Thr Asn Ala Asn Ser Lys Thr Gly Arg Glu Asn Val Ser
            340                 345                 350

Ala Arg Val Ser Cys Asp Asp Gly Glu Thr Trp Pro Gly Val Arg Thr
        355                 360                 365
```

```
Ile Arg Ser Gly Phe Ser Ala Tyr Ser Thr Val Thr Arg Leu Ala Asp
    370                 375                 380

Gly Lys Phe Gly Val Leu Tyr Glu Gly Asn Tyr Thr Asp Asn Met Pro
385                 390                 395                 400

Phe Ala Thr Phe Asp Asp Ala Trp Leu Asn Tyr Val Cys Ala Pro Leu
                405                 410                 415

Ala Val Pro Ala Val Asn Ile Ala Pro Ser Ala Thr Gln Glu Val Pro
            420                 425                 430

Val Thr Val Thr Asn Gln Glu Ala Thr Thr Leu Ser Gly Ala Thr Ala
        435                 440                 445

Thr Val Tyr Thr Pro Ser Gly Trp Ser Ala Thr Thr Val Pro Val Pro
    450                 455                 460

Asp Val Ala Pro Gly Ala Ser Val Thr Val Thr Val Ala Leu Thr Ala
465                 470                 475                 480

Pro Ala Asp Ala Ser Gly Pro Arg Ser Leu Asn Ala Ala Phe Thr Thr
                485                 490                 495

Ala Asp Gly Arg Val Ser Gln Phe Thr Phe Thr Ala Thr Thr Pro Val
            500                 505                 510

Ala Pro Gln Val Gly Leu Thr Ile
            515                 520

<210> SEQ ID NO 2
<211> LENGTH: 1563
<212> TYPE: DNA
<213> ORGANISM: Artificial Sequence
<220> FEATURE:
<223> OTHER INFORMATION: Nucleic acid sequence encoding the catalytic
      domain of the Arthrobacter ureafaciens sialidase.

<400> SEQUENCE: 2
atggctacag gctcccggac gtccctgctc ctggcttttg gcctgctctg cctgccctgg     60
cttcaagagg gatccgcccc cactccgccc aattcgccca cgcttccacc gggcagcttc    120
tctgaaacca atctggcggc cgaccgcacg gcggcgaatt tcttctaccg gattcccgcg    180
cttacctacc ttggcaacga cgtggtcctt gcagcgtggg acggtcgccc gggttcggcg    240
gcggacgccc cgaacccgaa ctcgatcgtc cagcgccgaa gcacggacgg tggcaagacc    300
tgggggccgg tccaagtgat cgccgcaggc acgtcgccg atgccagcgg ccctcgatac    360
ggctacagcg atccctcgta catctacgac gcggaagcca acaaggtctt cgctttcttc    420
gtgtactcga aggaccaagg ctttggcggc agtcagttcg caacgacga cgcggaccgg    480 aacgtcattt cctccgccgt catcgagtct ccgacgccg gcgtgacatg gagccagccc    540
cgcctcatca cctccgtcac caagccgggt accagcaaga ccaacccggc agccggcgac    600
gtccgctcca actttgcctc ctccggtgag ggcatccagc tcaaatacgg cccgcacaag    660
ggccgtctca tccagcagta cgccggcgac gtgcggcaag ctgacggaag caacaagatc    720
caggcctaca gcgtctattc agacgatcac ggcgtcacgt ggcacaaggg tgccaacgtg    780
ggcgaccgga tggacgagaa caagactgtg aactgtccg acggtcgggt cctgctcaac    840
tcccgggaca cgccaaccg gggctaccgc aaggtggccg tctccacgga cggcggagcc    900
acgtacggcc ccgtcagcca ggacacggaa ttgccggacc ctgccaacaa cggtgcaatc    960
gcccgcatgt tccccaacgc ggcgcagggc tccgcagacg cgaagaaact gatcttcacc   1020
aacgcaaact ccaagaccgg ccgcgaaaac gtctcggccc gggtctcctg tgacgacggc   1080
gaaacctggc cgggcgtccg caccatccgt tccggcttct cggcctactc aacagtgacc   1140
```

-continued

| | | | | |
|---|---|---|---|---|
| cgcctggcgg | acggaaagtt | cggcgtcctc | tacgagggca | actacacgga | caacatgccc | 1200 |
| ttcgccacct | tcgacgacgc | gtggttgaac | tacgtctgcg | ctcccttggc | agtaccggca | 1260 |
| gtcaacatcg | ccccgagcgc | aacgcaggag | gttccggtga | ccgtcactaa | ccaggaagca | 1320 |
| accacgcttt | ccggcgcgac | cgcaactgtc | tatacgccgt | cggggtggtc | tgccaccacg | 1380 |
| gtgcccgtgc | ccgacgtcgc | ccccggcgcg | tccgtcaccg | tgaccgttgc | actgaccgca | 1440 |
| ccggcggacg | ccagtggccc | gcgcagcctc | aacgcggcat | tcacgacggc | ggatggccgg | 1500 |
| gtttcgcagt | tcaccttcac | cgccaccacg | cccgtggctc | cgcaagtggg | ccttaccatc | 1560 |
| tag | | | | | | 1563 |